United States Patent
Wu

(10) Patent No.: US 8,628,809 B2
(45) Date of Patent: Jan. 14, 2014

(54) **METHOD OF INDUCING MUCOSAL IMMUNE RESPONSE TO ANTIGEN WITH *DIOSCOREA* POLYSACCHARIDES ADJUVANT**

(75) Inventor: Rong-Tsun Wu, Taipei (TW)

(73) Assignee: National Yang-Ming University, Taipei (TW)

( * ) Notice: Subject to any disclaimer, the term of this patent is extended or adjusted under 35 U.S.C. 154(b) by 605 days.

(21) Appl. No.: 12/430,353

(22) Filed: Apr. 27, 2009

(65) Prior Publication Data

US 2009/0258034 A1 Oct. 15, 2009

Related U.S. Application Data

(60) Continuation-in-part of application No. 11/093,970, filed on Mar. 29, 2005, now abandoned, which is a division of application No. 10/160,670, filed on May 30, 2002, now Pat. No. 6,998,262.

(51) Int. Cl.
| | |
|---|---|
| *A61K 36/00* | (2006.01) |
| *A61K 39/12* | (2006.01) |
| *A61K 39/02* | (2006.01) |
| *A61K 45/00* | (2006.01) |
| *A61K 47/00* | (2006.01) |

(52) U.S. Cl.
USPC ..... 424/773; 424/725; 424/204.1; 424/278.1; 424/234.1

(58) Field of Classification Search
None
See application file for complete search history.

(56) References Cited

U.S. PATENT DOCUMENTS 5,118,673 A * 6/1992 Carpenter et al. ............. 514/54
2003/0224066 A1 * 12/2003 Wu ............................... 424/725

OTHER PUBLICATIONS

Tomoda et al. Plant Mucilages. Isolation and Characterization of a Mucilage, *Dioscorea-mucilage* B from the rhizophors of *Dioscorea batatas*. Chem Pharm Bull. 29 (11) . 1981. 3256-3261.*

* cited by examiner

*Primary Examiner* — Chris R Tate
*Assistant Examiner* — Russell Fiebig
(74) *Attorney, Agent, or Firm* — Volpe and Koenig, P.C.

(57) ABSTRACT

A method for inducing mucosal immune responses in a subject in need thereof to an antigen includes administering to the subject a vaccine composition including the antigen and a *Dioscorea* polysaccharides as an adjuvant. Because of the immuomodulatory effect of the *Dioscorea* polysaccharides, the vaccine composition is further capable of breaking immunological tolerance in the subject.

10 Claims, 24 Drawing Sheets

METHOD OF INDUCING MUCOSAL IMMUNE RESPONSE TO ANTIGEN WITH *DIOSCOREA* POLYSACCHARIDES ADJUVANT

CROSS-REFERENCE TO RELATED APPLICATIONS

The present application is a continuation in part of co-pending U.S. patent application Ser. No. 11/093,970, filed Mar. 29, 2005, which is a division of U.S. patent application Ser. No. 10/160,670, filed May 30, 2002, now U.S. Pat. No. 6,998,262, issued Feb. 14, 2006, the disclosures of each of which are hereby incorporated by reference herein in their entireties.

FIELD OF THE INVENTION

The present invention relates to a method of inducing a mucosal immune response to an antigen in a subject in need thereof comprising administering to the subject a vaccine composition comprising the antigen, and a *Dioscorea* polysaccharides component as an adjuvant.

BACKGROUND OF THE INVENTION

Yam is the common name for some of the several *Dioscorea* species (*Dioscorea* sp.) within the genus *Dioscorea*, a member of the monocotyledonous family Dioscoreacea, and is a staple food in West Africa, Southeast Asia, and the Caribbean. Yam has very high nutritional value, for example, it is high in vitamin C, dietary fiber, vitamin B6, potassium, and manganese, which may all promote good health, while being low in saturated fat, sodium, and cholesterol.

*Dioscorea* has been studied for years for their medicinal effects. In the Chinese pharmacopoeia, the medicinal uses of *Dioscorea* rhizome are prescribed for indigestion, anorexia, diarrhea and diabetes. Recently several species are known to be pharmacologically active against hypertension, heart disease and other physical ailments (Chen, H. L., et al., Nutrition, 19: 646-651, 2003). Moreover, yam tuber mucilage was reported to exhibit antioxidant ability (Hou, W. C. et al., *J. Agric. Food Chem.* 49: 4956-4660, 2001).

In recent years, the medicinal effect of *Dioscorea* polysaccharides also has been studied and published. In the *Journal of China Pharmaceutical University,* 25(6):369-72, 1994, it was reported that *Dioscorea* polysaccharides decreased, in vitro, the NADPH-Vc induced and cysteine-$Fe^{2+}$ induced malondialdehyde formation of brain, liver and kidney microsomes in rats, and scavenged superoxide radicals generated by the hypoxanthine/xanthine oxidase reaction system and Fenton reaction system. Therefore, *Dioscorea* polysaccharides seem to be used as an antioxidant and superoxide radical scavenger. In the *Journal of Plant Resources and Environment,* 5(2):5-8, 1996, it is illustrated that the content of polysaccharide and allantoin of *Dioscorea* tuber have a remarkable effect on lowering the sugar and lipid levels in blood.

The mucous membranes covering the aerodigestive and the urogenital tracts, as well as the eye conjunctiva, the inner ear and the ducts of all exocrine glands are endowed with powerful mechanical and chemical cleansing mechanisms that degrade and repel most foreign matter. In addition, a large and highly specialized innate and adaptive mucosal immune system protects these surfaces, and thereby also the body interior, against potential insults from the environment. In a healthy human adult, this local immune system contributes almost 80% of all immunocytes. These cells are accumulated in, or in transit between, various mucosa-associated lymphoid tissues (MALT), which together form the largest mammalian lymphoid organ system (Dahan, S. et al., *Immunol. Rev.* 215: 243-253, 2007).

As for the importance of the mucosal system, there is currently great interest in developing mucosal vaccines against a variety of microbial pathogens, for the following reasons: (1) the vast majority of infections occur at or enter the body from a mucosal surface; (2) mucosal vaccines would also carry less risk of transmitting the type of infections still associated with the use of injectable vaccines in several parts of the world, such as hepatitis B virus and HIV infections; (3) oral vaccine administration could lead to simplified manufacturing of vaccines, thereby increasing the potential for local vaccine production in developing countries (Holmgren, J. et al., *Vaccine* 21: Suppl 2:S89-S95, 2003).

However, to date, except for oral polio vaccine, there is still no good mucosal vaccine that has been developed. Oral tolerance is one of the characteristics of the mucosal system, but is also the biggest obstruction for the vaccine development (Eriksson, K. et al., *Curr. Opin. Immunol.* 5: 666-672, 2002). Cholera toxin and *E. coli* heat-labile enterotoxin are the best-studied and most potent mucosal adjuvants up to the present. Unfortunately, they are also highly toxic to humans (Holmgren, J. et al., supra). Accordingly, it is important to find a better mucosal adjuvant. The present invention satisfies this need.

SUMMARY OF THE INVENTION

The present invention is based on the discovery of *Dioscorea* polysaccharides having an effect on the enhancement of mucosal immune responses, and therefore being a good candidate as an adjuvant for a mucosal (such as oral or nasal) vaccine.

Accordingly, the present invention relates to a method of inducing mucosal immune responses to an antigen in a subject in need thereof comprising administering to the subject a vaccine composition comprising the antigen, and a *Dioscorea* polysaccharides component as an adjuvant, wherein the *Dioscorea* polysaccharides component is characterized by a FT-IR (Fourier transform infrared) spectrum with peaks at 3000-2850 $cm^{-1}$, 1050-1020 $cm^{-1}$, 1085-1075 $cm^{-1}$, 1155-1150 $cm^{-1}$ and 845-830 $cm^{-1}$, and is prepared by a process comprising:

(a) eliminating small molecules by immersing *Dioscorea* sp. in a 30% (v/v) to 100% (v/v) alcoholic solution to obtain an insoluble solid portion;

(b) de-starching the insoluble solid portion obtained in (a) in a water solution by a starch hydrolyzing enzyme to obtain an aqueous solution;

(c) treating the aqueous solution obtained in (b) with a 30% (v/v) to 100% (v/v) alcoholic solution to obtain a precipitated solid portion; and (d) removing all protein substances from the precipitated solid portion obtained in (c) with a deproteinizing agent.

BRIEF DESCRIPTION OF THE DRAWINGS

The foregoing summary, as well as the following detailed description of the invention, will be better understood when read in conjunction with the appended drawings. It should be understood, however, that the invention is not limited to the precise arrangements and instrumentalities shown.

In the drawings.

DETAILED DESCRIPTION OF THE INVENTION

This present invention is based on the discovery of the effect of *Dioscorea* polysaccharides in inducing or enhancing mucosal immune responses, which are potent when used as a mucosal adjuvant.

Accordingly, the present invention relates to a method of inducing mucosal immune responses to an antigen in a subject in need thereof comprising administering to the subject a vaccine composition comprising the antigen, and a *Dioscorea* polysaccharides component as an adjuvant.

Figure 1A:
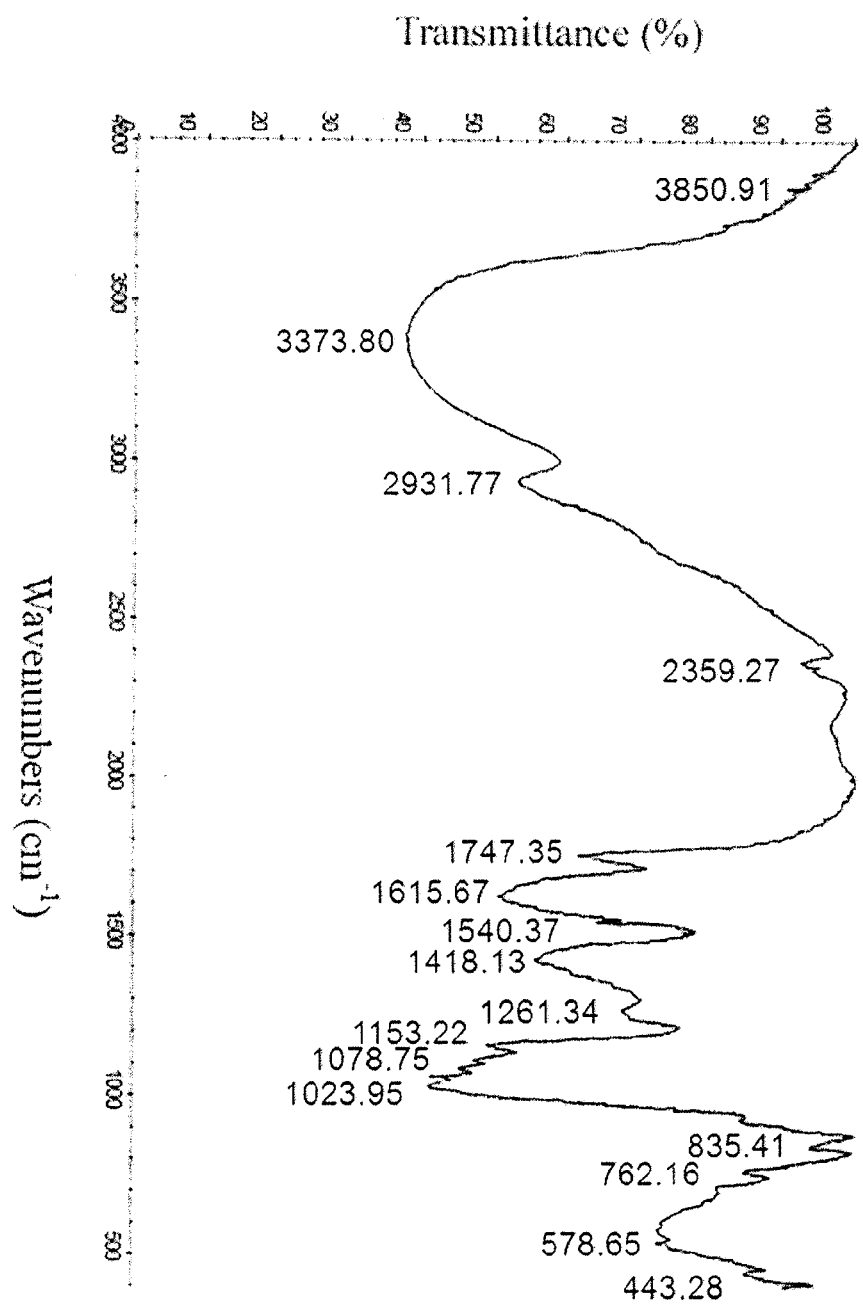
FIGS. 1A-1C are Fourier Transform Infrared (FTIR) spectrographs of *Dioscorea* polysaccharides extracted from the species *Dioscorea alata* L. cv. Phyto, *Dioscorea japonica* and *Dioscorea alata* L. var. Tainung No. 1, respectively, based on the method set forth in Example 1.
Figure 1B:
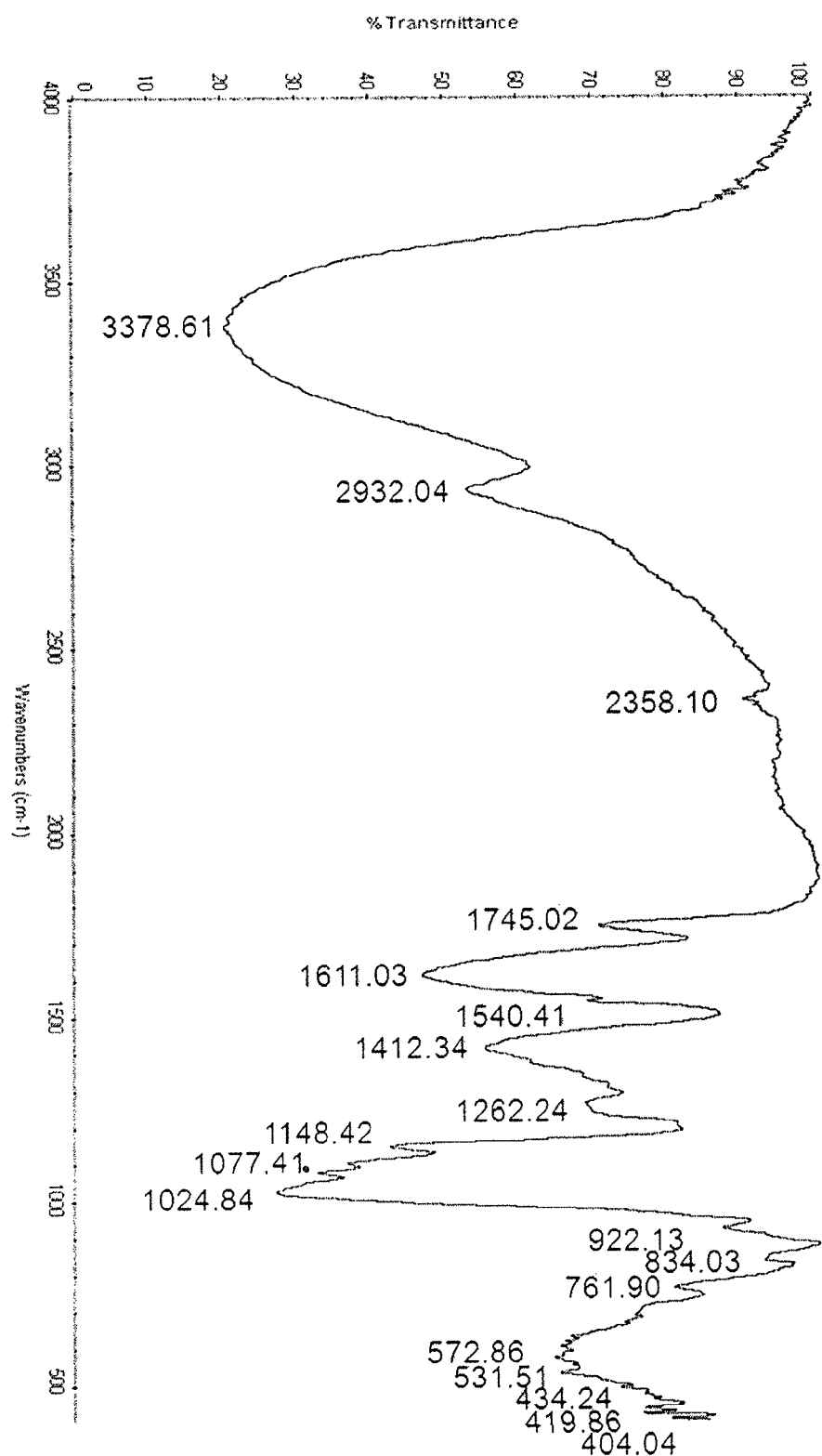
Figure 1C:
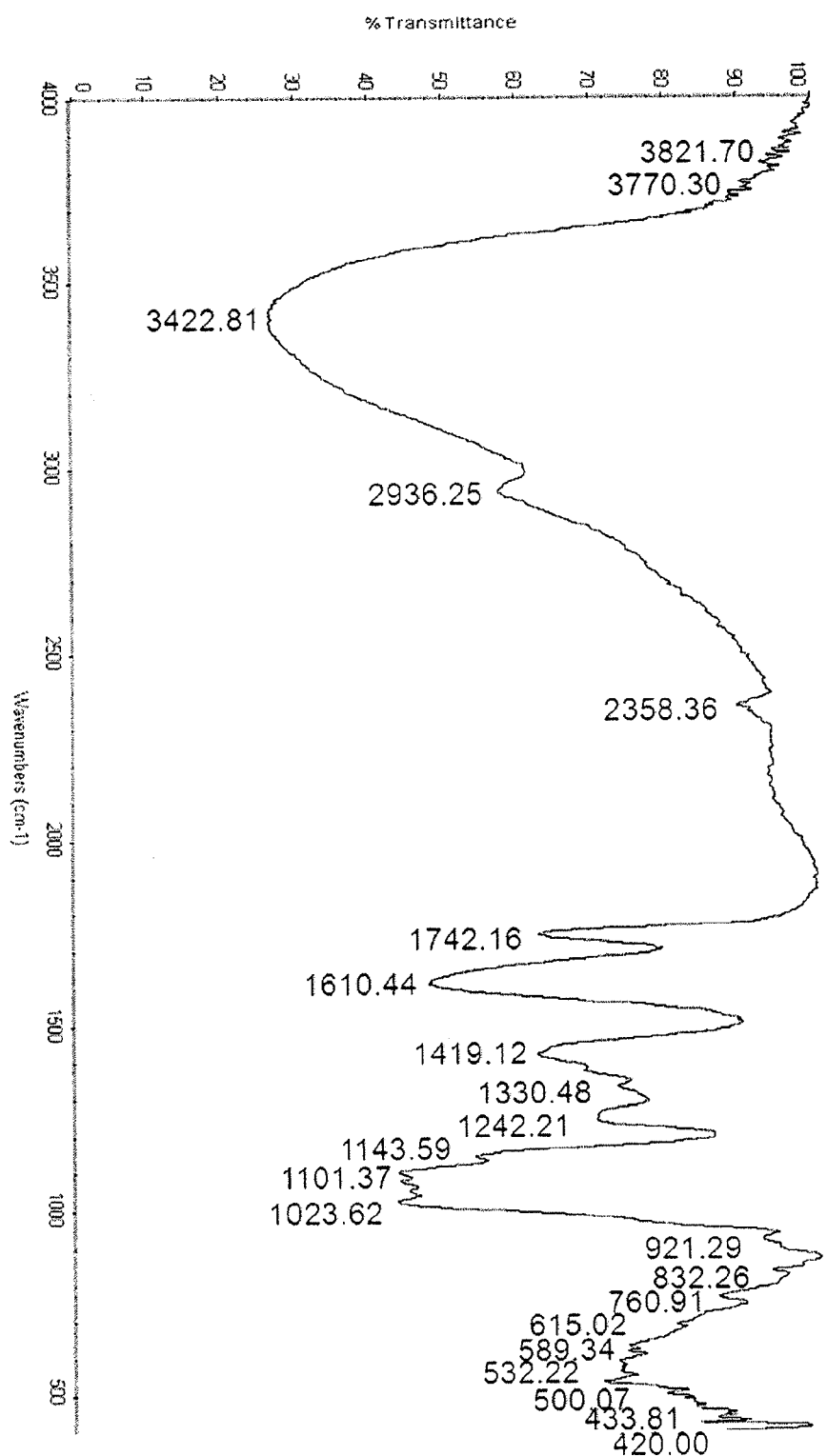

As used herein, the term "*Dioscorea* polysaccharides" or "*Dioscorea* polysaccharides component," which are used synonymously, refers to a mixture of polysaccharides, which has a FT-IR (Fourier transform infrared) fingerprint substantially as characterized in FIGS. 1A, 1B or 1C, wherein the FT-IR fingerprint is recorded in KBr with a spectrometer, exhibiting absorption in the region of 3000-2850 $cm^{-1}$, 1050-1020 $cm^{-1}$, 1085-1075 $cm^{-1}$, 1155-1150 $cm^{-1}$ and 845-830 $cm^{-1}$. In one example of the invention, the *Dioscorea* polysaccharides component is a mixture of polysaccharides, which has a FT-IR fingerprint substantially as characterized in FIG. 1A. According to the invention, the *Dioscorea* polysaccharides or *Dioscorea* polysaccharides component are prepared by a process comprising:

(a) eliminating small molecules by immersing *Dioscorea* sp. in a 30% (v/v) to 100% (v/v) alcoholic solution to obtain an insoluble solid portion;

(b) de-starching the insoluble solid portion obtained in (a) in a water solution by a starch hydrolyzing enzyme to obtain an aqueous solution;

(c) treating the aqueous solution obtained in (b) with a 30% (v/v) to 100% (v/v) alcoholic solution to obtain a precipitated solid portion; and (d) removing all protein substances from the precipitated solid portion obtained in (c) with a deproteinizing agent.

*Dioscorea* polysaccharides may be extracted from all kinds of *Dioscorea* sp. It was found that the polysaccharides extracted from various species of *Dioscorea* had similar FT-IR fingerprints. In the embodiment of the present invention, *Dioscorea* polysaccharides may be extracted from *Dioscorea* sp., including *Dioscorea alata* and *Dioscorea japonica*. In the non-limiting examples of the invention, *Dioscorea* polysaccharides may be extracted from *Dioscorea alata* L. cv. Phyto or *Dioscorea alata* L. var. Tainung No. 1.

According to the invention, to prepare *Dioscorea* polysaccharides, the tubers of *Dioscorea* sp. were collected and then immersed into a 30% (v/v) to 100% (v/v) alcoholic solution (such as methanol or ethanol) followed by a separation, so as to obtain an insoluble solid portion. In one example (Method A), the peeled tubers were immersed into 40% (v/v) methanol or ethanol. In another example (Method B), the peeled and dried tubers were immersed into 100% (v/v) methanol or ethanol.

Any one skilled in the art may use any standard method or a well known or commonly used method or starch hydrolyzing enzyme to perform the de-starching step. For example, the insoluble solid portion as obtained in the previous step may be de-starched by a starch hydrolyzing enzyme in a water solution. The term "a water solution" or "aqueous solution" used herein refers to a solution containing water as a solvent, such as water or distilled water. In one example of the invention, the starch hydrolyzing enzyme is α-amylase, preferably in an amount of about 0.6% by weight and starch hydrolyzing may be carried out at an elevated temperature, such as at about 80° C.

After de-starching, a further purification was conducted. The aqueous solution obtained in step (b) was mixed with a 30% (v/v) to 100% (v/v) alcoholic solution (such as methanol, or ethanol) to obtain a precipitated solid portion. In one example, the aqueous solution obtained in step (b) was mixed with 50% (v/v) ethanol to obtain a precipitated solid portion. In another example, the aqueous solution obtained in step (b) was mixed with 75% (v/v) ethanol to obtain a precipitated solid portion.

In another embodiment of the present invention, the process for preparing *Dioscorea* polysaccharides may comprise a further step of treating the polysaccharides extract with a deporteinizing agent so as to remove proteins therefrom. Any one skilled in the art may use any standard or commonly use or well known method to remove the proteins from the extracts. The deporteinizing agent may include but be not limited to chloroform and 1-butanol (1:3), trichloride acetic acid (3% v/v), HCl, 0.8% papain (w/v), and 1% tannalbin (w/v). One example of the deproteinizing agent is a mixture of chloroform and 1-butanol (1:3).

The term "vaccine" as used herein refers to a preparation of an antigen, which may be a weakened or killed pathogen, such as a bacterium or virus, or a portion of the pathogen's structure that upon administration stimulates antibody production or cellular immunity against the pathogen but is incapable of causing severe infection. The term "antigen" used herein refers to a substance that prompts the generation of antibodies and can cause an immune response. In the embodiment of the invention, the antigen may be a viral, a bacterium, or a fragment thereof, or a portion of a pathogen's structure. The virus, bacterium, or a portion of the pathogen's structure may be produced or isolated by traditional methods, or obtained commercially, both of which are recognized by one skilled in the art. Also, the vaccine may be prepared from commercial products. In one example of the invention, the antigen is hemagglutinin (HA), which is the major epitope of influenza virus. It is prepared by a commercial influenza vaccine (for instance, KKB/KI-Flu® vaccine, available from The Kitasato Institute, Japan). In another example of the invention, the antigen is *Pneumococcus* in a vaccine such as Pneumovax®23 (Merck & Co., Inc., West Point, Pa., USA), containing 23 of the most prevalent *Streptococcus pneumoniae*.

The term "adjuvant" used herein refers to a substance to be added to a vaccine composition to improve the immune response to the antigen so that less of the antigen is needed to produce a non-specific stimulator of the immune response, or a longer response or an enhanced response. According to the invention, it was found that *Dioscorea* polysaccharides may be used as a mucosal adjuvant, and particularly, an oral or nasal adjuvant for a vaccine composition, particularly an oral or intranasal vaccine composition.

According to the invention, the vaccine composition may be manufactured by any conventional (standard) or known methods by admixing the antigen and adjuvant with one or more pharmaceutically acceptable carriers. The term "pharmaceutically acceptable carrier" as used herein refers to a filler, a diluent, an encapsulating material or a formulation auxiliary that is non-toxic to subjects to which it is administered at the dosages and concentrations employed, and is compatible with other ingredients of the composition. A pharmaceutically acceptable carrier encompasses any of the standard pharmaceutical carriers suitable for a vaccine, particularly a mucosal vaccine. Such carriers may include, but be not limited to, saline, buffered saline, dextrose, water, glycerol, ethanol and combinations thereof.

According to the present invention, the vaccine composition comprises *Dioscorea* polysaccharides as a mucosal adjuvant in an effective amount. The phase "effective amount" as used herein refers to an amount that produces an enhanced effect of the antigen used with the adjuvant in the composition, when used at a dosage sufficient to produce a desired result, namely, in an amount to generate a mucosal or systemic immune response, such as enhancing antibody production, in the subject to which it is administered. It is apparent to anyone skilled in the art to use an appropriate amount to produce an effect in enhancing the immune response of the antigen, determined by different administered routes, or physiology of the subject in need, by routine experimentation based on the effect empirically noted when using various amounts.

The appropriate dose of a composition according to the present invention to be administered to a subject depends on the subject to be treated, such as the general health of the subject, the age of the subject, the nature of the infectious agents against which the subject is to be immunized, and the weight of the subject. Again, the dosage which would be appropriate would be apparent to one of skill in the art as determined by routine experimentation based on the effect empirically noted when using various dosages.

The frequency of administration of the composition can be administered in a single or, more typically, multiple doses, including booster doses over a period of time. Preferred frequency for a given composition is readily determinable by those of skill in the art by a variety of means, such as through routine trials establishing dose response curves. It will alternatively, as the dosage, be determined by the care giver based on age, weight, anticipated infectious agent, health status and patient responsiveness. Similarly, the frequency of administration would be apparent to one of skill in the art as determined by routine experimentation based on the effect empirically noted when dosing at various frequencies.

According to the invention, the vaccine composition comprising an antigen and *Dioscorea* polysaccharides as an adjuvant could induce mucosal immune responses to the antigen. The term "mucosal site" as used herein refers to oral, buccal, esophageal, gastric, endometrial, nasal, lung, respiratory tract, ocular, intestinal and/or vaginal sites. In one example of the invention, the mucosal site is any one of nasal, lung, respiratory tract, ocular, intestinal and vaginal sites. As compared to a systemic immune response, a good mucosal response can effectively prevent systemic infections, since a stimulation of this mucosal immune response can result in production of protective B and T cells in both mucosal and systemic environments so that infections are stopped before they get into the interior of the body past the mucosal cells. Accordingly, mucosal vaccines have been developed and are more widely accepted by the public because they have several advantages over traditional systemic vaccines, such as they may be administered by a nasal or oral route, instead of the administration by injection as commonly used, which is disadvantageous in either of the practical and immunological aspects. For example, a vaccine by injection for which needles, syringes and a trained injector are required, are more expensive and unpopular with recipients because it is painful to take the injection. The immunological drawback with the injection is that the route of injection is not the usual one of entry of the majority of pathogens against which the vaccination is directed, because many pathogens initially invade the host via the mucosal surfaces.

Antigenic exposure at mucosal sites activates mucosal B and T-lymphocytes to migrate from the inductive site and home to various mucosal effective sites. The common mucosal immune system involves homing of antigen-specific lymphocytes to mucosal effective sites other than the site where initial antigen exposure occurred. Different immunization routes, such as oral, rectal, and intranasal, can induce generalized mucosal immune responses. According to one example of the invention, a mucosal immune response, e.g., antigenic specific IgA or IgG antibody was induced or enhanced at a plurality of mucosal sites, wherein the mucosal site includes a site selected from the group consisting of oral, buccal, esophageal, gastric, endometrial, nasal, lung, respiratory tract, ocular, intestinal and/or vaginal sites, and particularly nasal, lung, respiratory tract, ocular, intestinal and/or vaginal sites.

To confirm whether the effect of *Dioscorea* polysaccharides on immunological activity is through the regulation of cytokine gene expression, mice were administered *Dioscorea* polysaccharides orally with food-intake for three days. The effect of *Dioscorea* polysaccharides on gene expression of cytokines, particularly IL-2, IFN-γ, IL-4, IL-5, IL-6, IL-10, and TGF-β was analyzed by RT-PCR. The results are shown in FIGS. 2 and 3.

Figure 2:
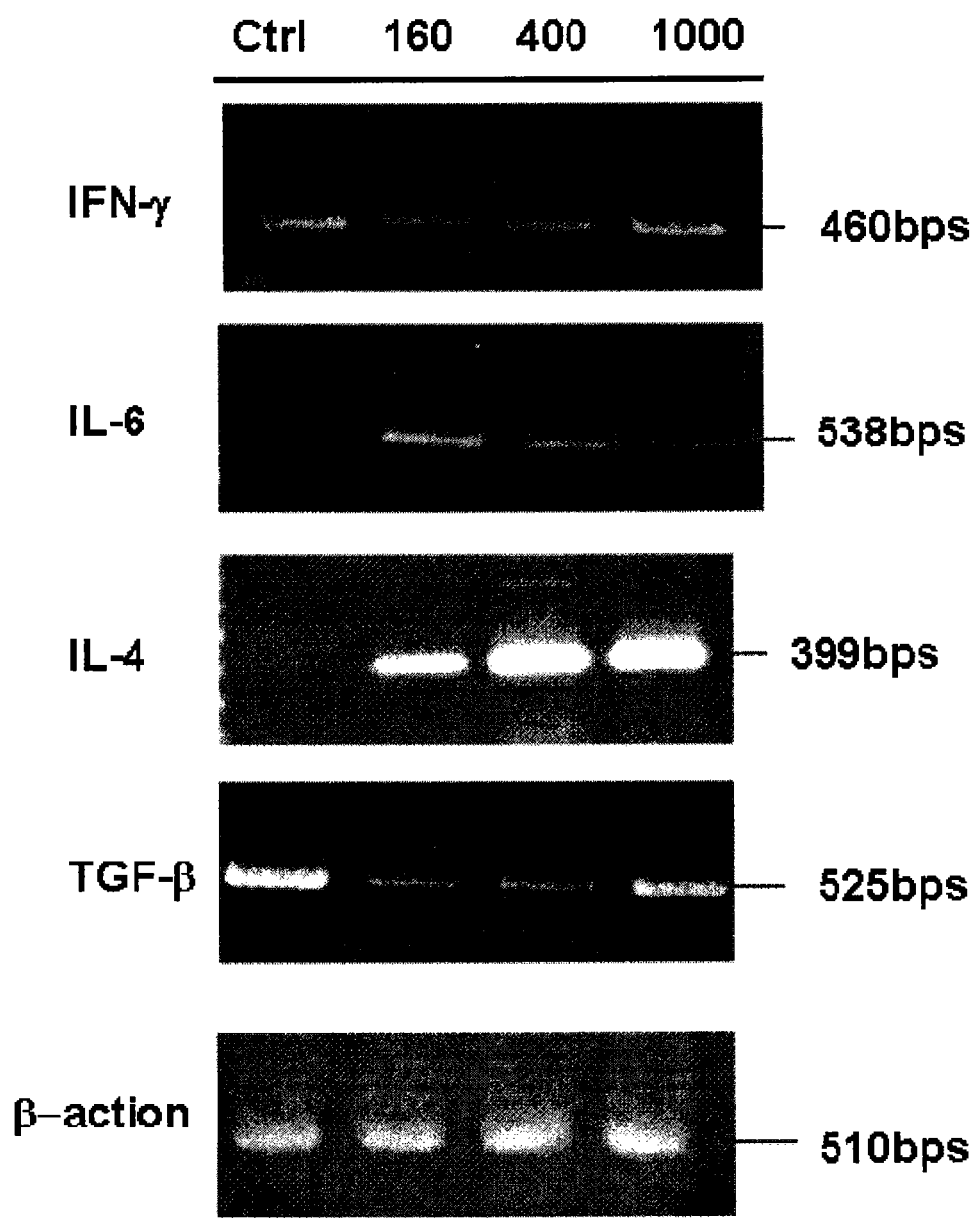
FIG. 2 is an image showing the RT-PCR result of cytokines in Peyer's patch isolated from mice to which were orally administered the *Dioscorea* polysaccharides according to the present invention.
Figure 3:
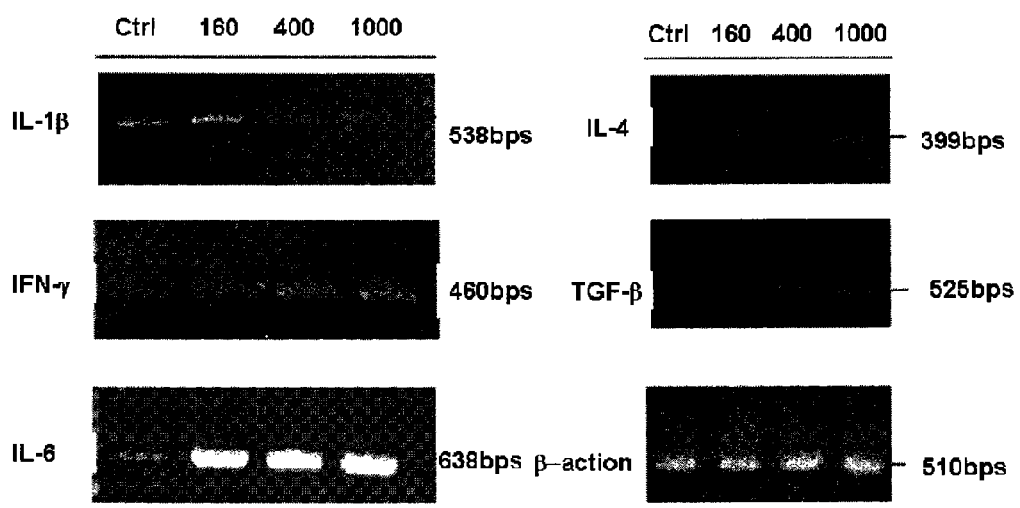
FIG. 3 is an image showing the RT-PCR result of cytokines in lamina propria isolated from mice to which were orally administered the *Dioscorea* polysaccharides according to the present invention.

As shown in FIG. 2, the gene expressions of IFN-γ, IL-4, and IL-6 in Peyer's patch increased, especially IL-4. In lamina propria, as shown in FIG. 3, the gene expression of IFN-γ, IL-4, IL-6, and TGF-β increased, especially IL-6. The results suggest that the *Dioscorea* polysaccharides prepared by the method of this invention can modulate the immunological response by regulating the cytokine expression. According to the invention, B cells were activated and the antibodies were increasingly secreted because of the gene expression of IL-4 and IL-6, IgM was conversed into IgA because of the gene expression of TGF-β in lamina propria.

Traditionally, antibodies measured in the blood are used as a marker for protection. Besides serum, as mentioned before, mucosal sites contain considerable lymphoid tissue, with lymphocytes aggregates within the lamina propria, all potentially capable of secreting immunoglobulins into the epithelial lining fluid (ELF). Diffusion from vascular compartments represents another source of immunoglobulins in ELF. Therefore, antibodies measured in the ELF lavaged from mucosal sites are alternatively used as a marker for protection.

From the experimental results of FIGS. 4A-10, it was unexpectedly found that the effect of the orally administered *Dioscorea* polysaccharides extract, which is prepared by the method of this invention, on mucosal (intestinal and pulmonary) IgA level and serum IgG level induced by orally immunizing with Pneumovax 23® was evidently enhanced. From the experimental results of FIGS. 15A-16D, both serum and mucosal IgA and IgG level were significantly increased in the mice intranasally administered KKB/KI-Flu® and *Dioscorea* polysaccharides. It is concluded that *Dioscorea* polysaccharides can enhance the immunological effects of an antigen administered to a subject in need thereof and is capable of enhancing the systemic and mucosal IgA and IgG level so as to improve the first line of defense against a wide variety of pathogens. *Dioscorea* polysaccharides also offer a safer adjuvant for a mucosal vaccine composition than cholera toxin as an adjuvant in a conventional mucosal vaccine.

As used herein, the term "immunological tolerance" refers to an immune system's adaptation to external antigens characterized by a specific non-reactivity of the lymphoid tissues to a given antigen that in other circumstances would likely induce cell-mediated or humoral immunity, which is also called acquired or induced tolerance. In adults, tolerance may be induced by repeated administration of very large doses of antigen, or of small doses that are below the threshold required for stimulation of an immune response. Immunosuppression also facilitates the induction of tolerance. One of the most important forms of acquired tolerance is oral tolerance, which is the specific suppression of cellular and/or humoral immune reactivity to an antigen by prior administration of the antigen by the oral route. Oral tolerance is a big obstruction to the development of oral vaccines, while some effective mucosal adjuvants, such as cholera toxin, have potential danger of some side effects. However, according to the invention, *Dioscorea* polysaccharides as an effective mucosal adjuvant are non-toxic and safe without any side effects.

Surprisedly, it is found that *Dioscorea* polysaccharides can break immunological tolerance. In the experiments according to the invention, the mice were administered ovalbumin (OVA) as an extrinsic protein by oral route to produce an immunological tolerance. However, *Dioscorea* polysaccharides can increase the mucosal (intestinal and pulmonary) IgA level and serum IgM and IgG level induced by orally immunizing with ovalbumin in C57BL/6j mice and C3H mice, as shown in FIGS. 1A-14B. The results clearly illustrated that *Dioscorea* polysaccharides could inhibit the oral tolerance caused by extrinsic protein. Furthermore, as shown in FIGS. 2A-8, 13A-14B, the production of IgA, IgG and cytokine expression was enhanced by the addition of *Dioscorea* polysaccharides, which is evidence of *Dioscorea* polysaccharides' effect in breaking immunological tolerance.

The invention will now be described more specifically with reference to the following specific examples relating to particular, presently preferred embodiments. It should be noted that the following descriptions of preferred embodiments of this invention are presented herein for the purpose of illustration and description only; they are not intended to be exhaustive or to be limited to the precise form disclosed.

Example 1

Preparation of *Dioscorea* Polysaccharides from *Dioscorea alata*

(Method A)
4 kg peeled tubers of *Dioscorea alata* were immersed in 40% (v/v) methanol or ethanol optionally in the presence of 1% (v/v) acetic acid, and the mixture solution was allowed to stand overnight, and then subjected to centrifugation at 5,000 rpm for 1 hour (RPR9-2 rotor, HITACHI HIMAC SCR20B, Japan). The precipitate was mixed with water in the presence of 0.6% (w/v) α-amylase at 80° C. for 1 hour to decompose starch. A supernatant solution was obtained by centrifugation at 5,000 rpm for 1 hour (RPR9-2 rotor, HITACHI HIMAC SCR20B, Japan), and treated with 50% (v/v) ethanol to obtain a precipitated solid portion. The obtained precipitated solid portion was then treated with a solution of choloroform/1-butanol (1:3) to remove proteins, leaving an extract of polysaccharides. Thereafter, the polysaccharides extract was dialyzed against water by a dialysis bag with 3000 Da pore size. The polysaccharides-containing solution was then lyophilized and re-dissolved in the water to be used in Example 4 and 5.

Example 2

Preparation of a Polysaccharide Component from *Dioscorea alata*

(Method B)
4 kg peeled tubers of *Dioscorea alata* were dried. The dried tubers were immersed in 100% (v/v) methanol or ethanol to eliminate small molecules, and then allowed to stand overnight, and then subjected to centrifugation at 5,000 rpm for 1 hour (RPR9-2 rotor, HITACHI HIMAC SCR20B, Japan). The precipitate was mixed with water in the presence of 0.6% (w/v) α-amylase at 80° C. for 1 hour to decompose starch. A supernatant solution was obtained by centrifugation at 5,000 rpm for 1 hour (RPR9-2 rotor, HITACHI HIMAC SCR20B, Japan), and treated with 50% (v/v) ethanol to obtain a precipitated solid portion. The obtained precipitated solid portion was then treated with a solution of choloroform/1-butanol (1:3) to remove proteins, leaving an extract of polysaccharides. Thereafter, the extract of polysaccharides was dialyzed against water by a dialysis bag with 3000 Da pore size. The polysaccharides-containing solution was then lyophilized and re-dissolved in the water to be used in Example 3 and 6.

Example 3

FT-IR Spectrums of *Dioscorea* Polysaccharides

The term Fourier Transform Infrared Spectroscopy (FT-IR) refers to a fairly recent development in the manner in which the data are collected and converted from an interference pattern to a spectrum. By interpreting the infrared absorption spectrum, the chemical bonds in a molecule can be determined. Here, 5 mg of a sample of the polysaccharides obtained from each of *Dioscorea alata* L. cv. Phyto, *Dioscorea japonica* and *Dioscorea alata* L. var. Tainung No. 1 according the method as illustrated in Example 2, was taken and milled with potassium bromide (KBr) to form a fine powder. The powder was then compressed into a thin pellet and then analyzed by using a Thermo® Nicolit®-IR100 Spectrometer (Thermo Fisher Scientific Inc., USA). FT-IR absorption spectra were acquired between 4000 and 500 $cm^{-1}$, and the transmittance was 0-100%. The spectrograph presented is shown as FIGS. 1A-1C.

As shown in FIGS. 1A (*Dioscorea alata* L. cv. Phyto), 1B (*Dioscorea japonica*) and 1C (*Dioscorea alata* L. var. Tainung No. 1), the band in the region of 3400-3200 $cm^{-1}$ was due to the hydroxyl stretching vibration of the polysaccharides. The band in the region of 3000-2850 $cm^{-1}$ was due to C-H stretching vibration. The absorptions at 1050-1020, 1085-1075 and 1155-1150 $cm^{-1}$ indicated a pyranose form of sugars. The polysaccharides extracted from *Dioscorea* sp.

exhibited absorption at 845-830 cm$^{-1}$, suggesting an α-dominating configuration, and this showed that the polysaccharides consist of α-pyranoside. Given the above, it is indicated that *Dioscorea* polysaccharides of the present invention may obtained from different species of *Dioscorea* sp.

Example 4

Effect of *Dioscorea* Polysaccharides on Gene Expression of Cytokines

Isolation of Peyer's Patch Cells

*Dioscorea* polysaccharides were administered orally with food-intake (0, 160, 400, 1000 mg/Kg) for 3 days to mice. The mice were then sacrificed and small intestine was obtained. The obtained small intestine was placed in a dish containing 1×HBSS solution and Peyer's patch was cut off. The Peyer's patch was torn into small pieces by needles and tweezers, cells were obtained by filtration with No. 53 mesh and centrifugation, and cells (about 1-2×10$^7$) were re-suspended for RNA isolation.

Isolation of Lamina Propria Cells

The intestinal fragments from which the epithelium cells have been removed were placed in 10-15 mL complete medium containing RPMI, Hepes, 2-ME and FCS (fetal calf serum) so as to terminate the reaction of EDTA and DTT. The fragments were incubated in 40 mL complete medium with 30 units Collagenase I and 10 units Collagenase II at 37° C. for 60 minutes. The cells were filtered by glass wool and a No. 53 mesh filter, followed by centrifugation at 200×g for 5 minutes. The cell pellet was washed with 1×HBSS, and centrifuged with 70% (v/v) Percoll® material (Sigma-Aldrich) and 42% (v/v) Percoll® material (5 mL) at 2000 rpm for 20 minutes. The live cells at a middle layer were obtained, washed with 10 mL 1×HBSS, centrifuged and re-suspended at the concentration of 1-3×10$^6$ cells/mL for RNA isolation.

Reverse Transcription and Polymerase Chain Reaction of Cytokines

Total RNA was extracted from Peyer's patch cells and lamina propria cells by using an Ultraspec™ RNA isolation kit (Biotex Laboratories Inc, U.S.A.). 5 µg total RNA and 2.5 µg oligo dT were heated at 70° C. for 10 minutes, cooled to room temperature for 10 minutes, added with 4 µL 10 mM dNTP, 0.5 µL rRNasin, 1 µL (10 units) AMV (Avian Myeloblastosis virus) reverse transcriptase and the buffer of AMV (provided in the kit) to a final reaction volume of 26.5 µL. cDNA was obtained by reacting the previous reaction solution at 42° C. for 60 minutes and then at 90° C. for 5 minutes. 2.5 µL resultant cDNA was added with 0.5 µL 10 mM dNTP, 0.5 µL polymerase (2 units), 1 µL 10 µM targeted primers, and the buffer of polymerase (provided in the kit) to a final volume of 25 µL. PCR was performed for 30 cycles, and each cycle contained 45 seconds of denaturation at 94° C., 45 seconds of annealing at 63° C. and 1 min of extension at 72° C. The reaction products were visualized by electrophoresis in 2% (w/v) agarose gel. Sequences of the PCR primers are shown in Table 1. The experimental results are shown in FIGS. 2 and 3.

In FIG. 2, the gene expressions of IFN-γ, IL-4 and IL-6 in Peyer's patch are increased, especially IL-4; and in lamina propria, shown in FIG. 3, the gene expression of IFN-γ, IL-4, IL-6 and TGF-β are increased, especially IL-6. The results suggest that the *Dioscorea* polysaccharides prepared by the method of this invention may modulate the immunological response by regulating the cytokine expression. It may stimulate or activate macrophages and make the surface cells in the lumen of the intestine become better antigen presenting cells by increasing IFN-γ expression in lamina propria; may stimulate B cells activation and increase the secretion of antibodies by increasing the gene expression of IL-4 and IL-6; and stimulate the conversion of IgM into IgA by increasing the gene expression of TGF-β in lamina propria.

TABLE 1

| Cytokine | Sequence (5'-3') | SEQ ID NO |
|---|---|---|
| IL-1β | | |
| upstream | ATG GAC ACT GTT CCT GAA CTC AAC T | 1 |
| downstream | CAG GAC AGG TAT AGA TTC TTT CCT TT | 2 |
| IL-4 | | |
| upstream | ATG GGT CTC AAC CCC CAG CTA GT | 3 |
| downstream | GCT CTT TAG GCT TTC CAG GAA GTC | 4 |
| IL-6 | | |
| upstream | ATG AAG TTC CTC TCT GCA AGA GAC | 5 |
| downstream | CAC TAG GTT TGC CGA GTA GAT CTC | 6 |
| IFN-γ | | |
| upstream | TGA ACG CTA CAC ACT GCA TCT TGG | 7 |
| downstream | CGA CTC CTT TTC CGC TTC CTG AG | 8 |
| TGF-β | | |
| upstream | TGG ACC GCA ACA ACG CCA TCT ATG CCA TCT ATG AGA AAA CC | 9 |
| downstream | TGG AGC TGA AGC AAT AGT TGG TAT CCA GGG CT | 10 |
| β-actin | | |
| upstream | GAG TAC CTC ATG AAG ATC CT | 11 |
| downstream | CCA CAT CTG CTG GAA GGT GG | 12 |

Example 5

Enhancement of Antibody Response to Bacterial Polysaccharide Antigen and Ovalbumin by Oral Intake of *Dioscorea* Polysaccharides Oral Administration with Pneumovax 23®

C57B/6j mice at 10 and 20 weeks of age were used for this study and kept in a specific pathogen free environment in the Animal Center of National Yang-Ming University, Taiwan.

For long-term administration of *Dioscorea* polysaccharides, three days prior to inoculation, experimental groups (3 mice/group) were supplemented with *Dioscorea* polysaccharides at the doses of 0 (control group), 10, 50, 250 mg/kg/day in daily drink until the mice were sacrificed. Both the 10 and 20 weeks C57B/6j mice were administered a dose of 25 µg of Pneumovax 23® (Merck & Co., Inc. West Point, Pa., USA) by oral inoculation after neutralizing the gastric acid with 1.5% (w/v) sodium bicarbonate in 1×HBSS on Day 1. Pre-immune serum was obtained from eyes before supplementation with *Dioscorea* polysaccharides, and the serum samples were collected from eyes on Days 7 and 14. The mice were sacrificed on Day 15 and the intestinal tract and lung were obtained and flushed.

For short-term administration (10 weeks C57B/6j mice), *Dioscorea* polysaccharides at the doses of 0 (control group), 10, 50, 250 mg/kg/day in daily drink was merely supplemented on Days 0, 1, 7 and 8, and oral inoculation 25 µg of Pneumovax 23® was carried out on Days 1 and 8. Pre-immune serum was obtained from eyes before supplementation with *Dioscorea* polysaccharides, and serum samples were collected from eyes on Days 7, 14 and 21 after inoculation and the mice were sacrificed on Day 22 after oral inoculation and the intestinal tract and lung were obtained and flushed.

For co-treatment administration (10 weeks C57B/6j mice), *Dioscorea* polysaccharides at the doses of 0 (control group), 10, 50, 250 mg/kg/day with 25 µg of Pneumovax 23® in daily drink were supplemented on Days 1 and 8. Pre-immune serum was obtained from eyes before supplementation with *Dioscorea* polysaccharides, and serum samples were collected from eyes on Days 7, 14 and 21 after inoculation and the mice were sacrificed on Day 22 after oral inoculation and the intestinal tract and lung were obtained and flushed.

Oral Administration with Ovalbumin

C57B/6j and C3H mice at 20 weeks of age were used for this study and kept in a specific pathogen free environment in the Animal Center of National Yang-Ming University in Taiwan. Three days prior to immunization, experimental groups (3 mice/group) were supplemented with *Dioscorea* polysaccharides at the doses of 10 and 50 mg/kg/day for C57B/6j mice and at the doses of 10, 50, and 250 mg/kg/day for C3H mice in daily drink until the mice were sacrificed. Pre-immune serum was obtained from eyes before supplementation with *Dioscorea* polysaccharides. Oral immunization was carried out by administration of 20 mg ovalbumin in 500 µL of PBS on Days 1, 8 and 29. The serum samples were collected from eyes on Day 36 after immunization and then the mice were sacrificed on Day 37 to obtain and flushed the intestinal tract and lung.

Collection of the Flushing Solution from Intestinal Tract and Lung of Mice (1) From Intestinal Tract The intestine between the rectum and the end of the small intestine was obtained and placed in 6 mL enzyme inhibitor solution (0.01% (w/v) soybean trypsin inhibitor in 50 mM EDTA). The intestine was cut longitudinally and washed with enzyme inhibitor solution. The washing solution was placed in 50 mL tube and the tissue pieces were dispersed and shaken to make sure that the solution was homogeneous. The solution was centrifuged at 650×g for 10 minutes to obtain the supernatant. 30 µL 100 mM PMSF (phenylmethylsulphonyl fluoride) in 95% (v/v) alcohol was added into the supernatant and the mixture solution was centrifuged to collect the aqueous phase. 20 µL PMSF and 20 µL sodium azide (1% w/v) were added into the collection and the solution stood on ice for 15 minutes. The reactant was further mixed with 100 µl FCS and stored at −20° C.

(2) From Lung

The trachea of mice was flushed back and forth 5 times with 1 mL 1% (w/v) BSA solution by 1 mL syringe with a hose and all flushing solutions were collected and centrifuged at 8500 rpm for 10 minutes (KUBOTA KM-15200, Japan). The supernatant was collected and stored at −20° C.

Antibodies Analysis by ELISA 96-well microtiter plates were precoated with 50 µL diluted Pneumovax 23® (1 µL of Pneumovax 23® vaccine in 49 µL of PBS) or 100 µL ovalbumin solution (4 µg/mL in 50 mM sodium carbonate/bicarbonate buffer, pH 9.6) at 4° C. overnight. After washing three times with washing solution (Tween® 20 surfactant in PBS, 0.05% v/v), 200 µL PBS-BSA (1% BSA in PBS, w/v) was added into the wells and incubated at room temperature for 1 hour. After washing three times with washing solution, 100 µL tested plasma (diluted 100× with PBS-BSA), intestinal flushing solution or pulmonary flushing solution were added into wells and reacted at room temperature for 2 hours. Wells were then washed six times with 200 µL PBS containing 0.05% (v/v) Tween® 20 surfactant, added with 100 µL secondary antibody (goat-anti-mouse IgG or IgA or IgM conjugated with alkaline phosphatase) diluted 1000× with PBS-BSA, and reacted at room temperature for 2 hours. Wells were then washed six times with 200 µL washing solution (Tween® 20 surfactant in PBS, 0.05% v/v), followed by rinsing with 100 µL reaction buffer solution (diethaloamin buffer: 9.7% v/v diethaloamin and 0.01% v/v magnesium chloride, pH 9.8) and added with 100 µL reactant (p-nitrophenyl phosphate, 1 mg/mL in diethaloamin buffer) for color development. The reaction solution was reacted at room temperature for 10-20 minutes. Titers were then recorded by ELISA reader at an absorbance of 410 nm or 405 nm.

Figure 4A:
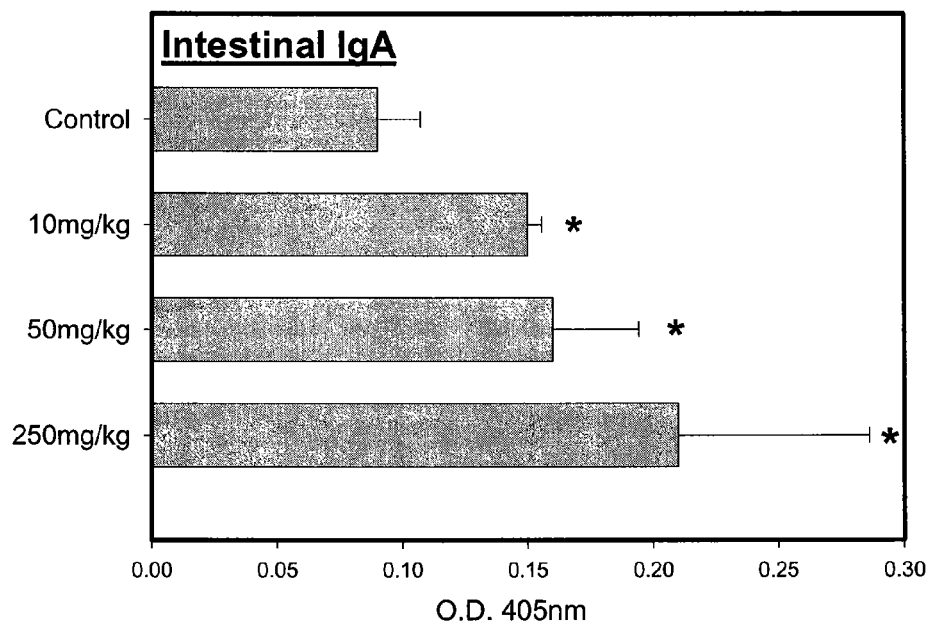
FIGS. 4A and 4B are bar graphs illustrating the Pneumovax 23® vaccine-specific IgA responses in intestinal lavage and pulmonary lavage, respectively, of 20 weeks C57BL/6j mice, which are induced by oral administration of *Dioscorea* polysaccharides of this invention.
Figure 4B:
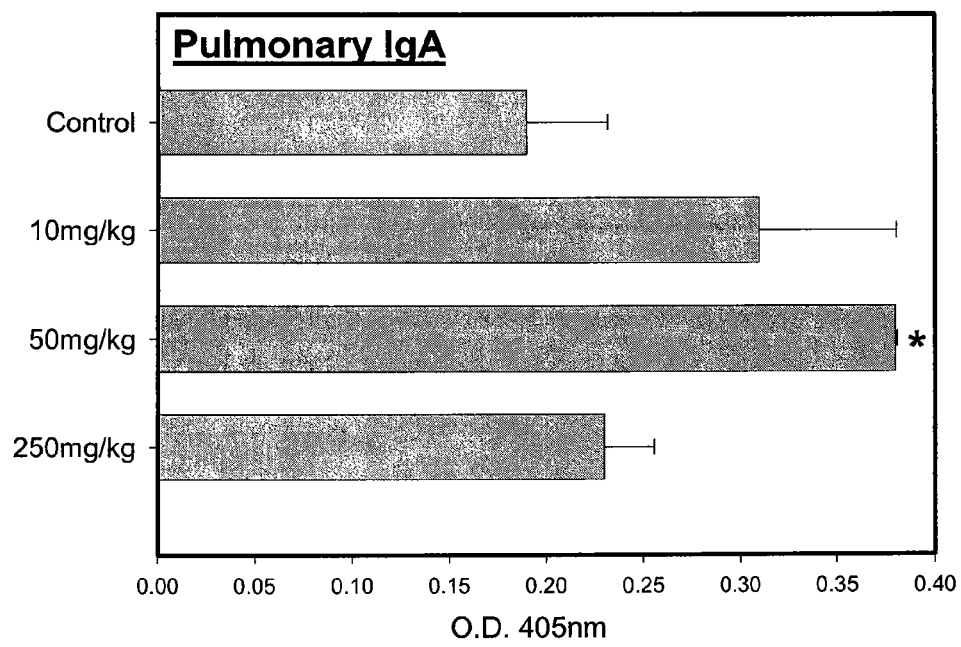
Figure 5A:
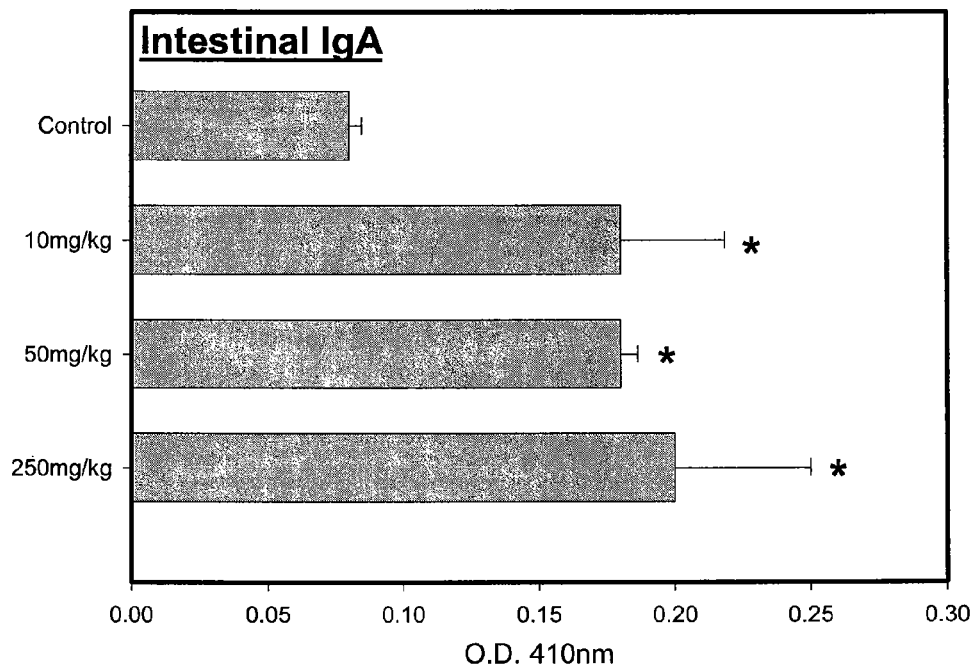
FIGS. 5A, 6A and 7A are bar graphs illustrating the Pneumovax 23® vaccine-specific IgA responses in intestinal lavage
Figure 5B:
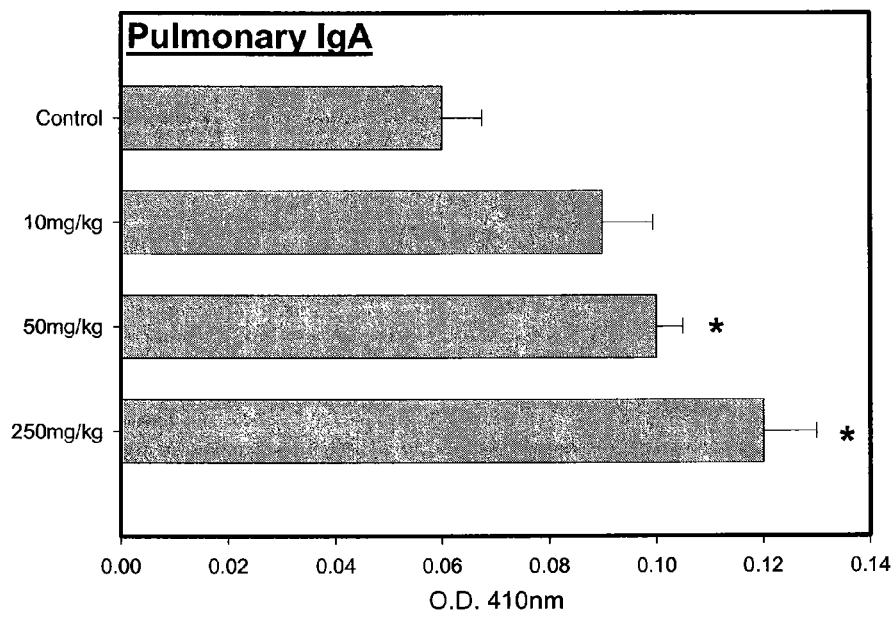
FIGS. 5B, 6B and 7B are bar graphs illustrating pulmonary lavage, respectively, of 10 weeks C57BL/6j mice, which are induced by oral *Dioscorea* polysaccharides of this invention.
Figure 6A:
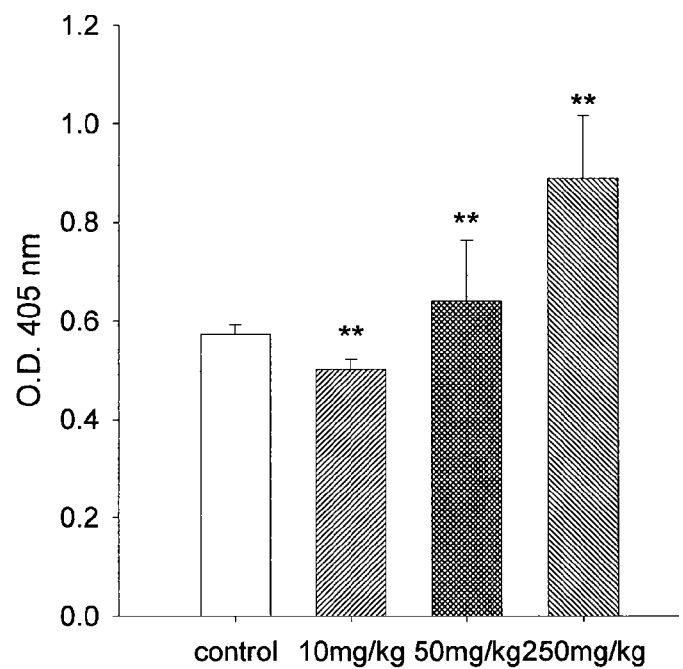
Figure 6B:
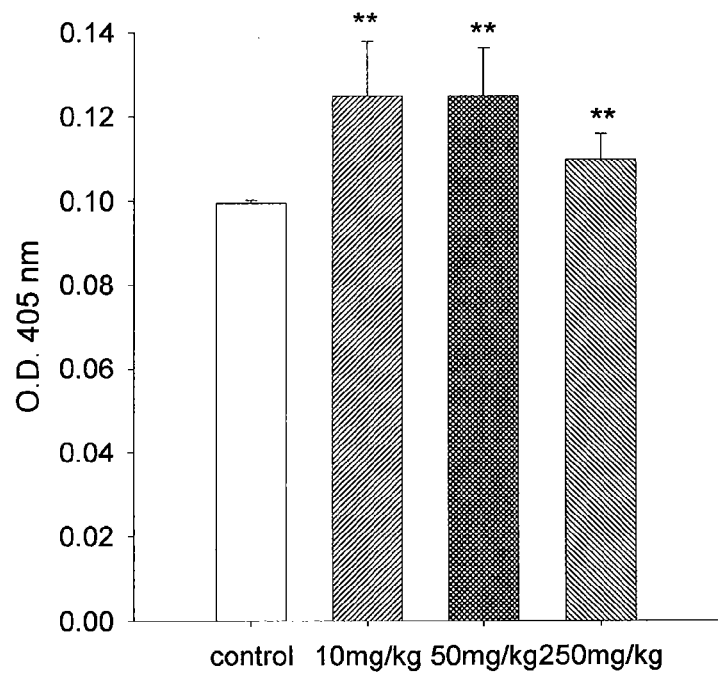

As shown in FIGS. 4A-6B, IgA titers of the 10 and 20 weeks C57BL/6j mice orally immunized with Pneumovax 23® vaccine were both significantly elevated by the orally active *Dioscorea* polysaccharides at the dose of 10-250 mg/Kg for long-term administration (as shown in FIGS. 4A and 5A) and 50-250 mg/Kg for short-term administration (as shown in FIG. 6A) in intestine, and at the dose of 50 mg/Kg for long-term administration (as shown in FIGS. 4B and 5B) and 10-250 mg/Kg for short-term administration (as shown in FIG. 6B) in lung. The IgA titer of the 10 weeks C57BL/6j mice orally immunized with Pneumovax 23® vaccine were also significantly elevated by the orally active *Dioscorea* polysaccharides at the dose of 250 mg/Kg for long-term administration (as shown in FIG. 6B) in lung.

Figure 7A:
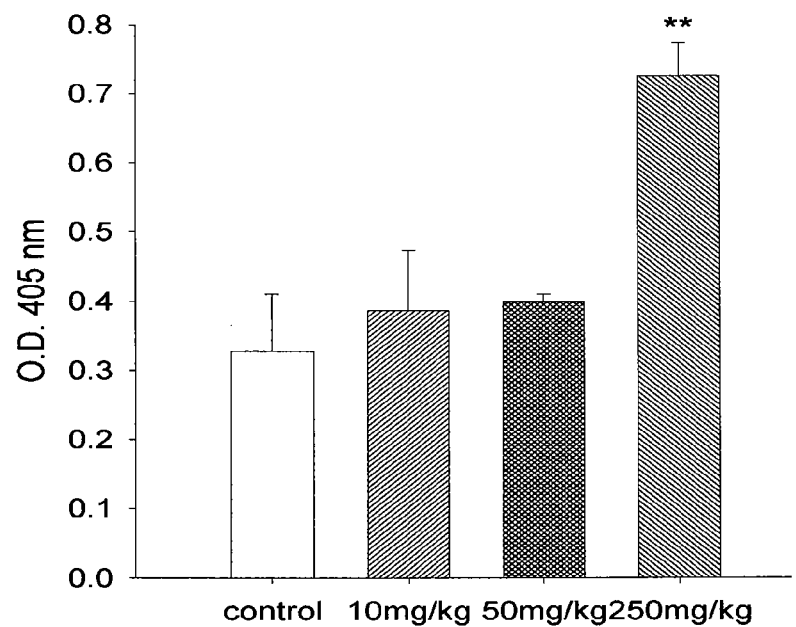
Figure 7B:
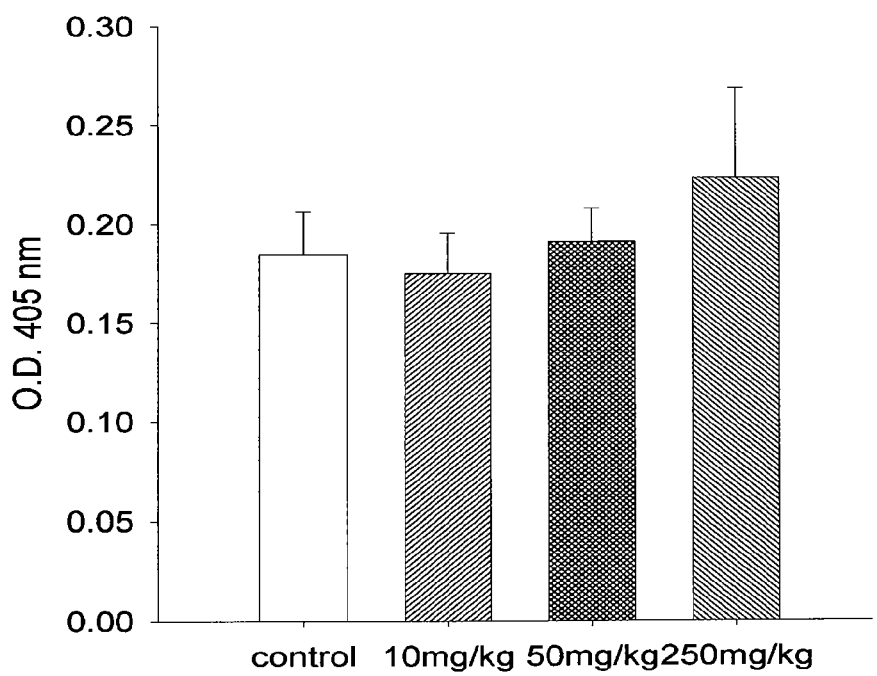

As shown in FIG. 7A, IgA titers of the 10 weeks C57BL/6j mice orally immunized with Pneumovax 23® vaccine were significantly elevated by the orally active *Dioscorea* polysaccharides at the dose of 250 mg/Kg for co-treatment in intestine.

Figure 8:
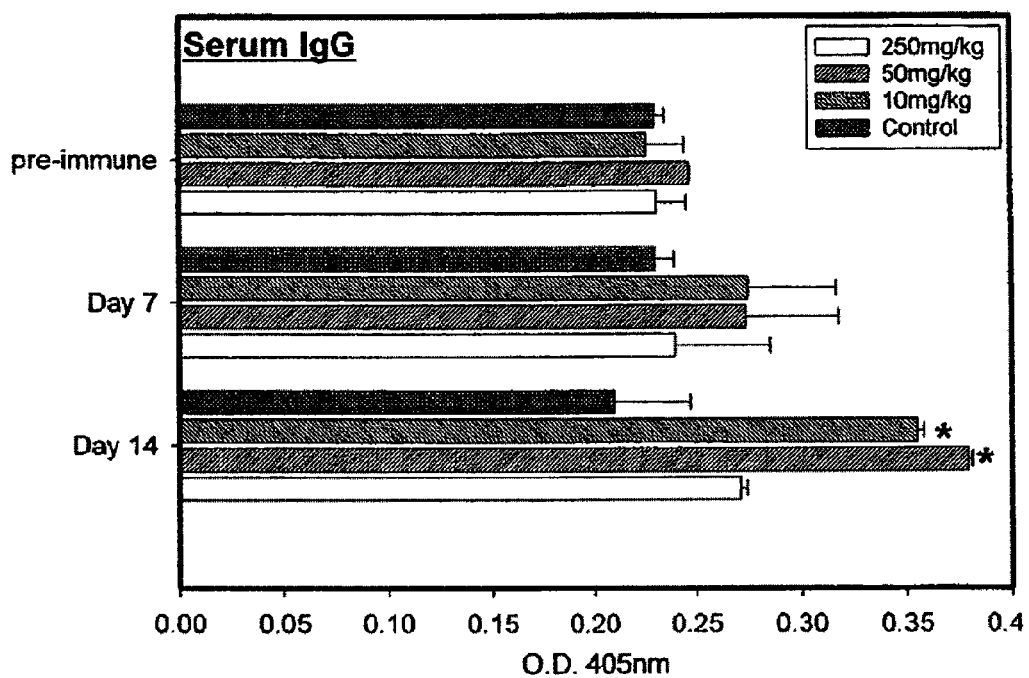
FIGS. 8, 9 and 10 are bar graphs illustrating the Pneumovax 23® vaccine-specific IgG responses in serum of the 10 weeks C57BL/6j mice, which are induced by oral *Dioscorea* polysaccharides of this invention.
Figure 9:
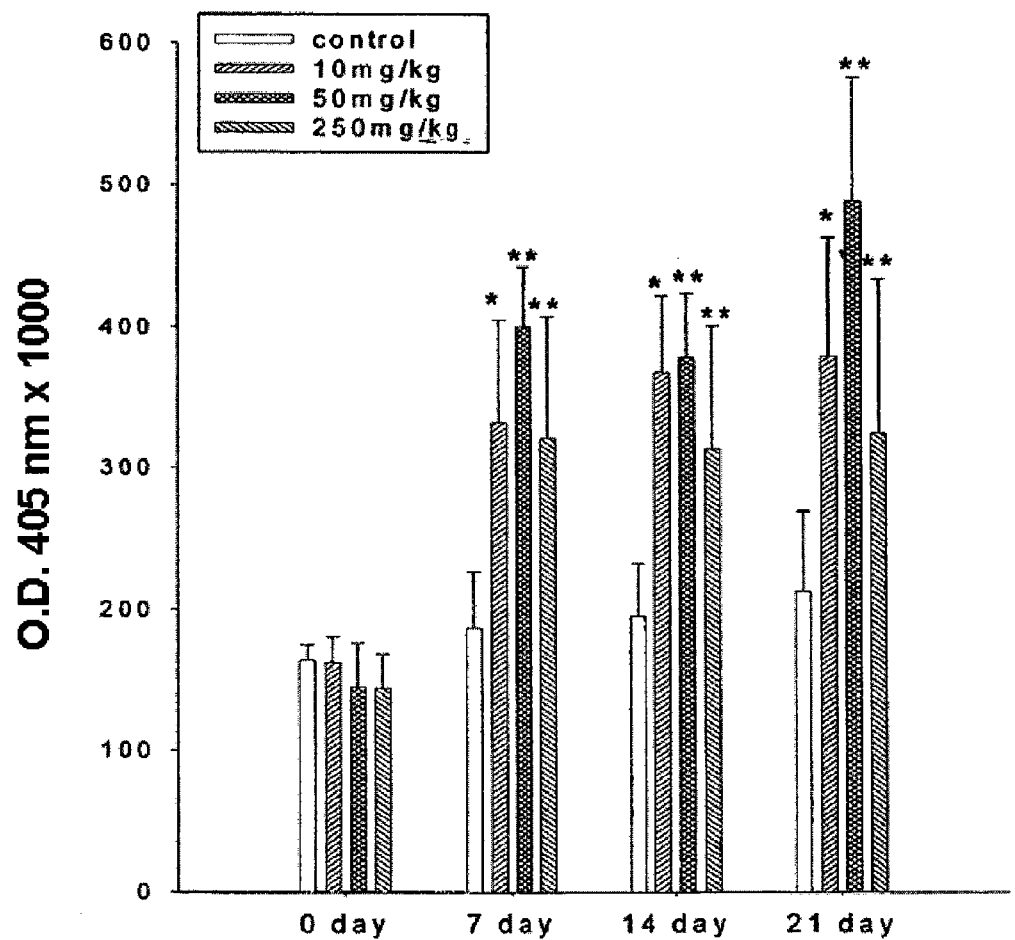

In FIGS. 8 and 9, serum IgG titers of the 10 weeks C57BL/6j mice orally immunized with Pneumovax 23® vaccine were significantly elevated by the orally active *Dioscorea* polysaccharides on Day 14 at the dose of 10-50 mg/Kg for long-term administration (FIG. 8) and on Days 7, 14 and 21 at the dose of 10-250 mg/Kg for short-term administration (FIG. 9).

Figure 10:
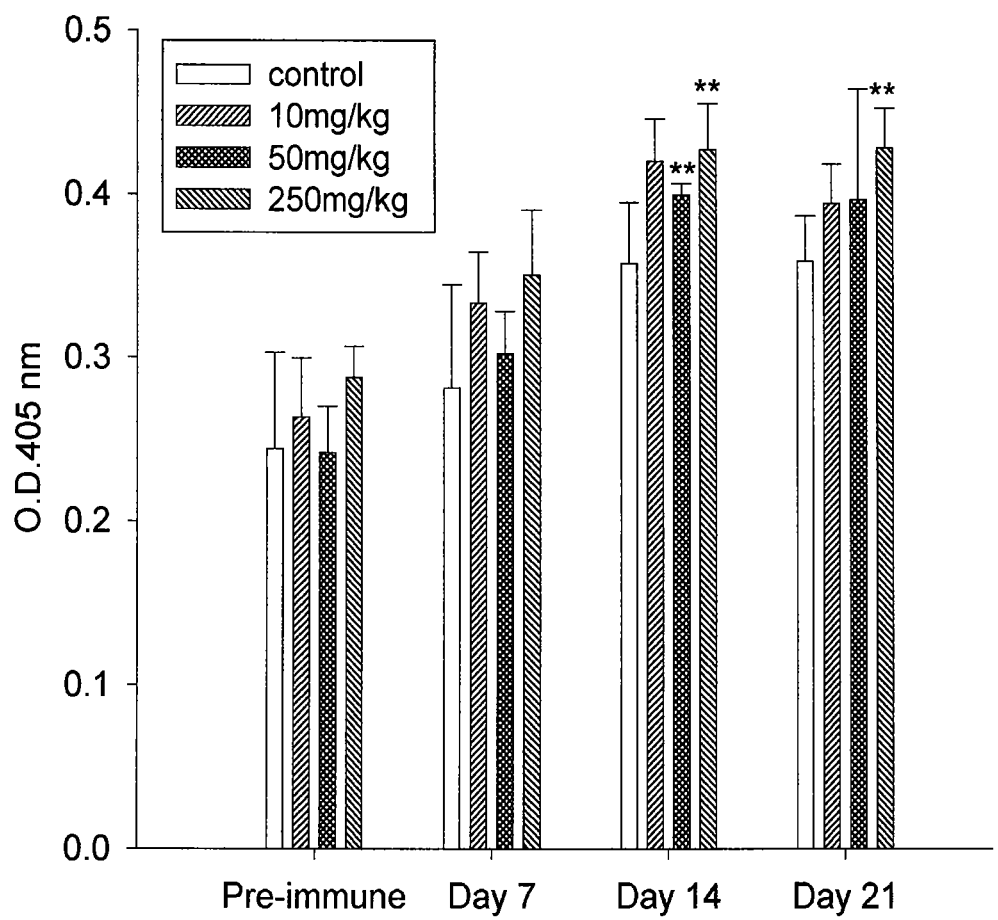

In FIG. 10, serum IgG titers of the 10 weeks C57BL/6j mice orally immunized with Pneumovax 23® vaccine were significantly elevated by the orally active *Dioscorea* polysaccharides on Day 14 at the dose of 50-250 mg/Kg, and on Day 21 at the dose of 250 mg/Kg for co-treatment. It indicated that antigenic specific antibody, both IgG in the serum and IgA in intestine and in lung, were induced or elevated when an antigen was orally administrated with *Dioscorea* polysaccharides (separately or concurrently) prepared by the method as showed in Example 1. These antibodies were released from B-cell activated by several regulatory cytokines as shown in Example 4.

Figure 11A:
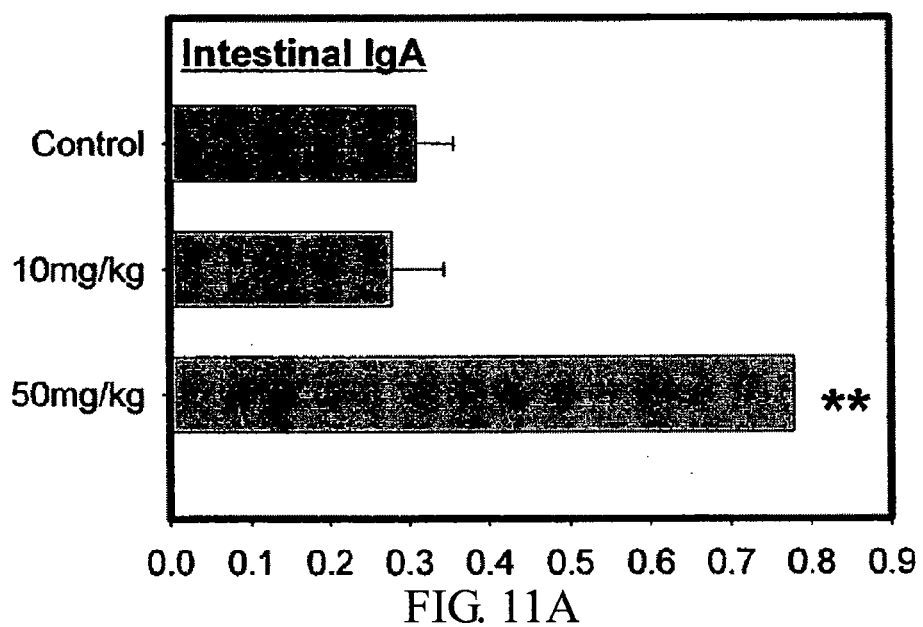
FIGS. 11A and 12A are bar graphs illustrating the ovalbumin (OVA)-specific IgA responses in intestinal lavage and FIGS. 11B and 12B are bar graphs illustrating pulmonary lavage, respectively, of the 20 weeks C57BL/6j mice and the 20 weeks C3H mice, which are induced by *Dioscorea* polysaccharides of this invention, to illustrate the ability of *Dioscorea* polysaccharides to break the oral tolerance.
Figure 11B:
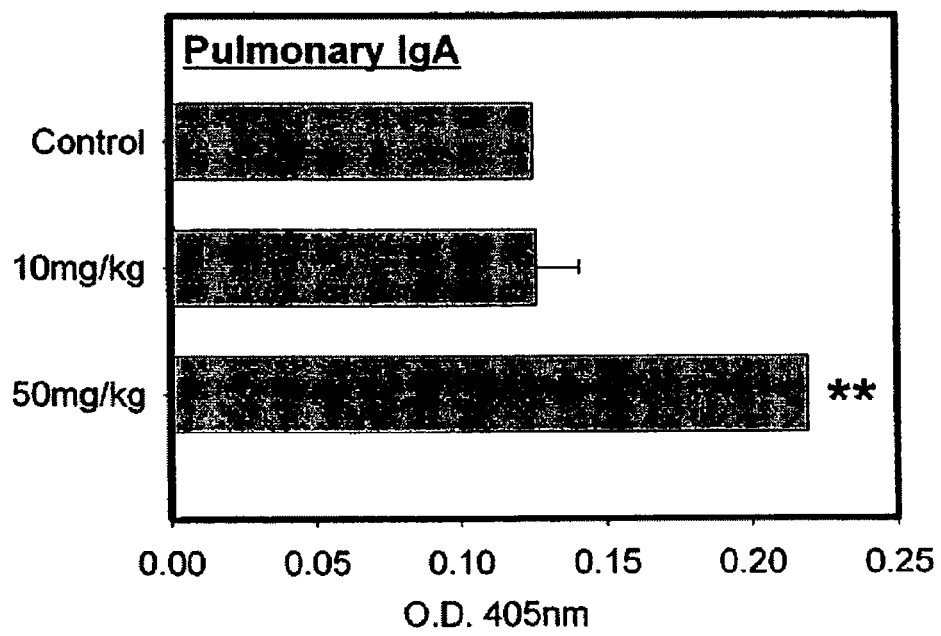
Figure 12A:
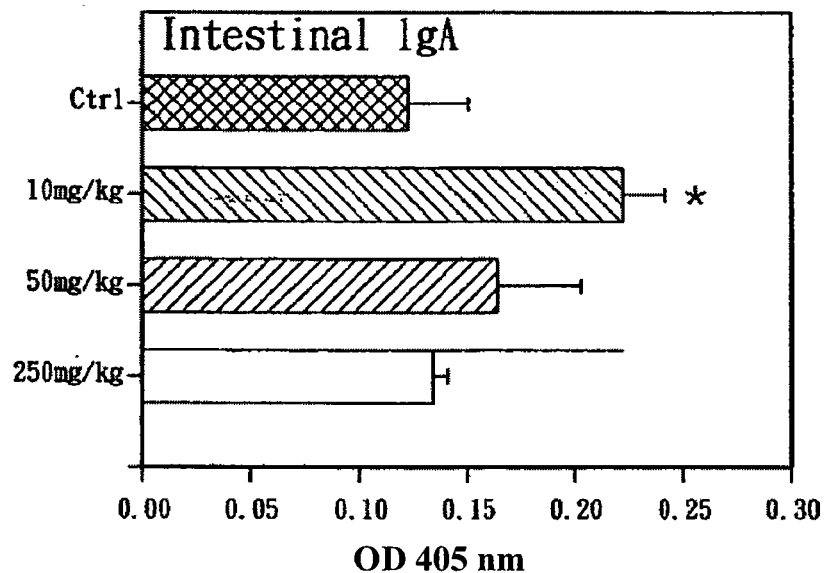
Figure 12B:
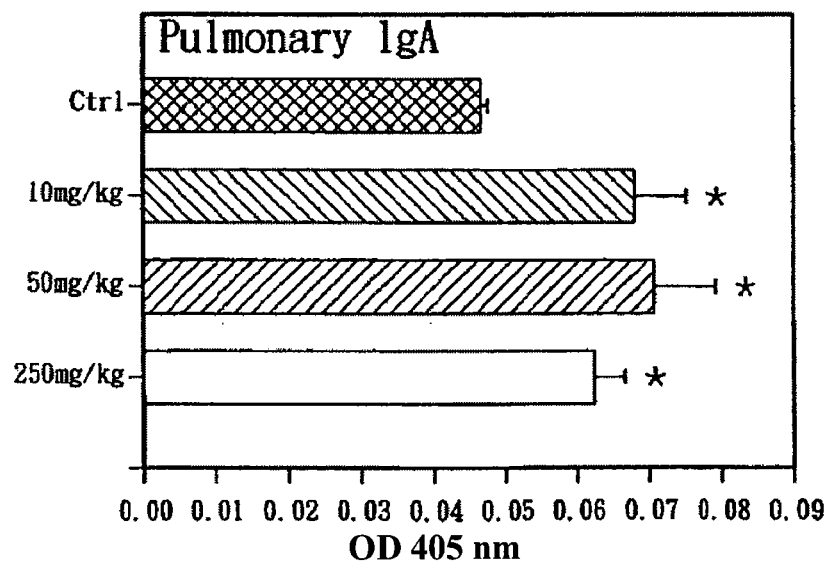
Figure 13A:
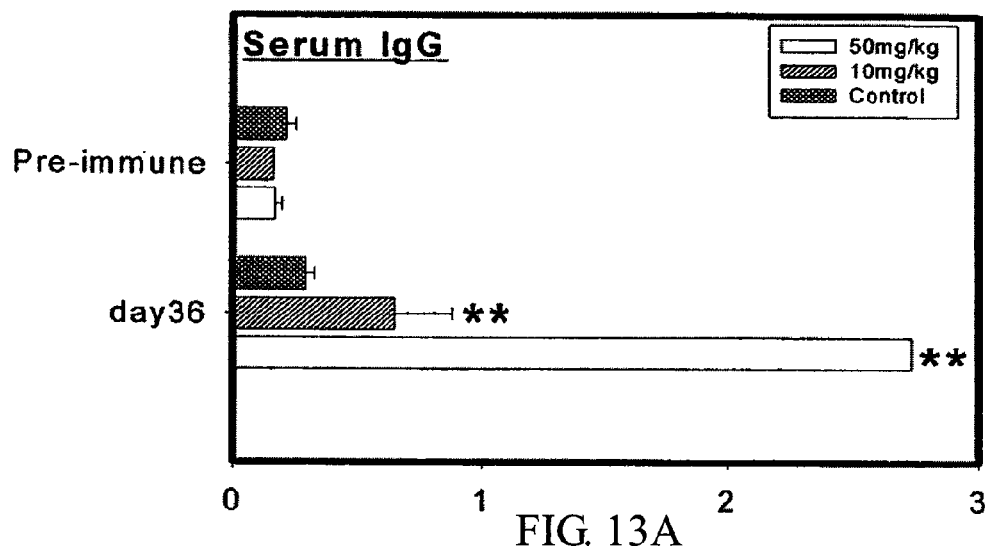
FIGS. 13A and 14A are bar graphs illustrating the IgG response.
Figure 13B:
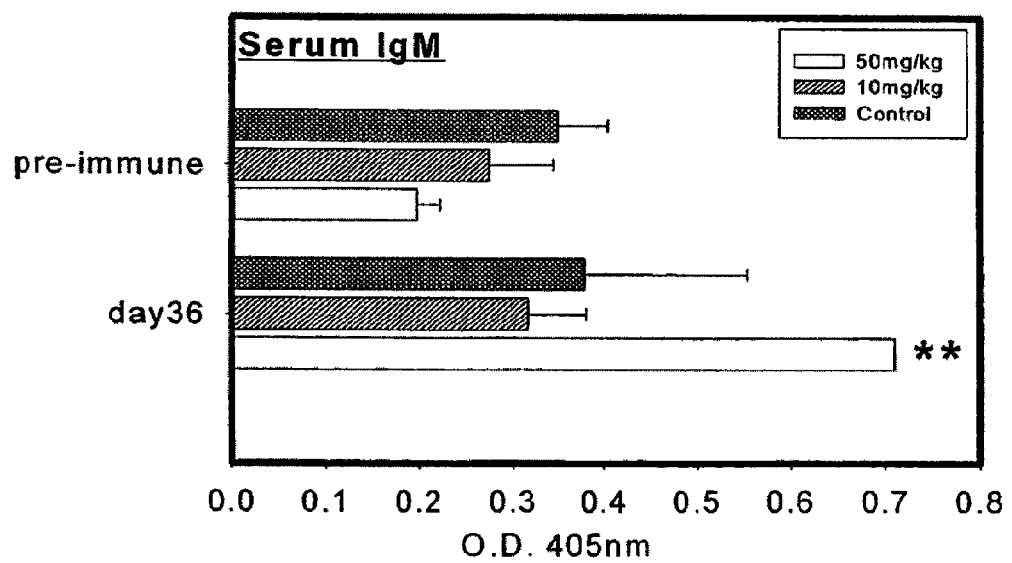
FIGS. 13B and 14B are bar graphs illustrating the IgM responses, respectively, in serum of the 20 weeks C57BL/6j mice and the 20 weeks C3H mice, which are induced by oral *Dioscorea* polysaccharides of this invention, to illustrate the ability of *Dioscorea* polysaccharides to break the oral tolerance.
Figure 14A:
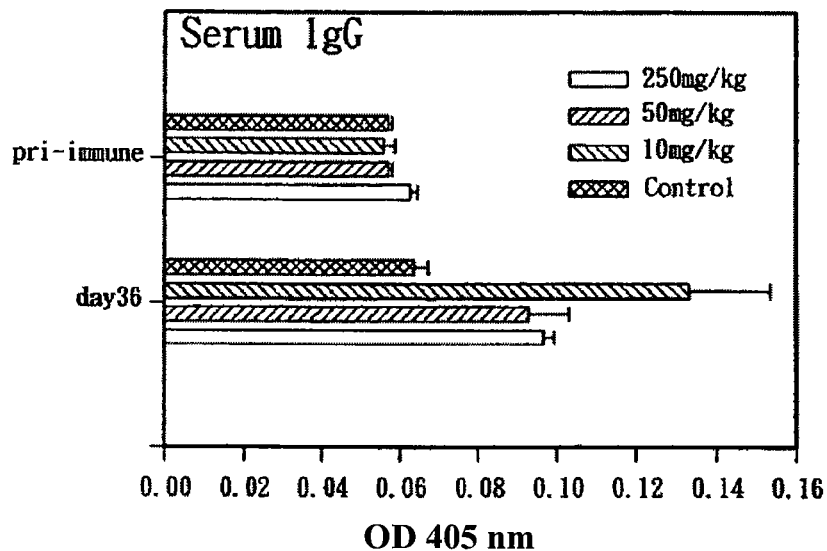
Figure 14B:
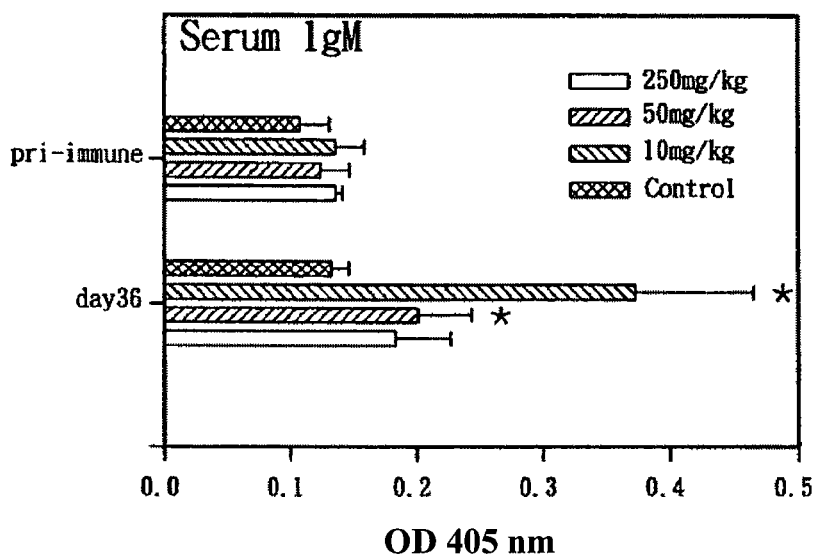

In FIGS. 11A and 11B, IgA titers in intestine and lung of the 20 weeks C57BL/6j mice orally administered with ovalbumin were significantly elevated by the orally-active *Dioscorea* polysaccharides at the dose of 50 mg/Kg. In FIGS. 12A and 12B, IgA titers of the 20 weeks C3H mice were significantly elevated at the dose of 10 mg/Kg in intestine and at the dose of 10-250 mg/Kg in lung. In FIGS. 13A and 13B, serum IgG titers of the 20 weeks C57BL/6j mice orally administered with Ovalbumin were significantly elevated by the orally active *Dioscorea* polysaccharides on Day 36 at the dose of 10-50 mg/Kg, and serum IgM titers were elevated on Day 36 at the dose of 50 mg/Kg. The elevating phenomenon was also found in 20 weeks C3H mice (see FIGS. 14A and 14B).

As shown in the results of FIGS. 11A-14B, the *Dioscorea* polysaccharides were proved to break oral tolerance and help the mucosal system to fully respond to the target antigen administered.

Example 6

Enhancement of Antibody Response to Influenza Virus Antigen by Nasal Intake of *Dioscorea* Polysaccharides Preparation of Vaccine and Immunization of Mice The vaccine used herein was KKB/KI-Flu® brought from ADImmune Corporation, otherwise called "Kuo Kwang Biotechnology Company" (Taichung, Taiwan), and it contained HA of the influenza virus species recommended by the World Health Organization/National Influenza Center for the period of 2005-2006, and includes an A/New Caledonia/20/99 (H1N1)-like virus, an A/California/7/2004(H3N2)-like virus and a B/Shanghai/361/2002-like virus. Each package was in a dosage of 0.5 mL/syringe and contained 15 μg HA.

Ten-weeks-old female Balb/c mice (H-$2^d$) were purchased from the National Laboratory Animal Center (Taipei, Taiwan). The mice were randomly grouped into a normal group (n=6, healthy mice, immunized by PBS), a control group (n=8, immunized by 1 μg HA), positive group (n=8, immunized by 4 μg HA), and the treatment group sensitized with adjuvant with a dose of 2 mg of *Dioscorea* polysaccharides (n=8, immunized by 1 μg HA) or 10 mg of *Dioscorea* polysaccharides (n=8, immunized by 1 μg HA) as set forth in Example 1.

Before sensitization, the mice were anesthetized by i.p. injection of Avertin (1.25% (w/v) tribromoethanol) with a dose of 0.25 g/Kg. The vaccine composition containing HA was administered intranasally by drops using a by 0.5 mL syringe according to the quantity of each group. The mice were boosted twice at ten day intervals with the same quantity for each group. On Day 30, all mice were sacrificed and blood, flushing solution from lung, nasal cavity and vaginal tract were collected for ELISA testing.

Antibodies Assays (ELISA)

Influenza subunit antigen-specific antibody responses were determined using an enzyme-linked immunosorbent assay (ELISA). Briefly, ELISA plates were coated overnight at 4° C. with 1 μg of HA per well in a coating buffer (0.05 M carbonate/bicarbonate, pH 9.6). The plates were washed and blocked by incubation with 2.5% (w/v) milk powder in the coating buffer for 2 hr at 37° C. Subsequently, the plates were washed with 200 μl PBS/Tween® surfactant (PBS containing 0.05% (v/v) Tween® surfactant pH 7.6). Appropriate dilutions of serum (1:100 for IgG, 1:25 for IgA) and vaginal wash (1:25 for IgG, 1:6 for IgA), and non-diluted nasal or lung lavages of each individual mouse were applied to the plates. Then the plates were incubated for 2 hr at 37° C. The plates were then washed six times and incubated with alkaline phosphatase-conjugated goat antibodies directed against either mouse IgG, or IgA (AP-conjugated IgG 1:4000, AP-conjugated IgA 1:2000) for 1 hr at 37° C. Thereafter, the plates were washed six times with PBS/Tween® surfactant. Specific antibodies were detected by staining with 100 μl substrate (1 mg/mL p-nitrophenylphosphate). Antibody titers are expressed as the reciprocal of the calculated sample dilution corresponding with an $A_{405}$ of 0.2 above the background. Comparison between different groups was made by a one-way analysis of variance (ANOVA) test.

Systemic and Local IgG and IgA Responses in intranasal Immunized Mice

Figure 15A:
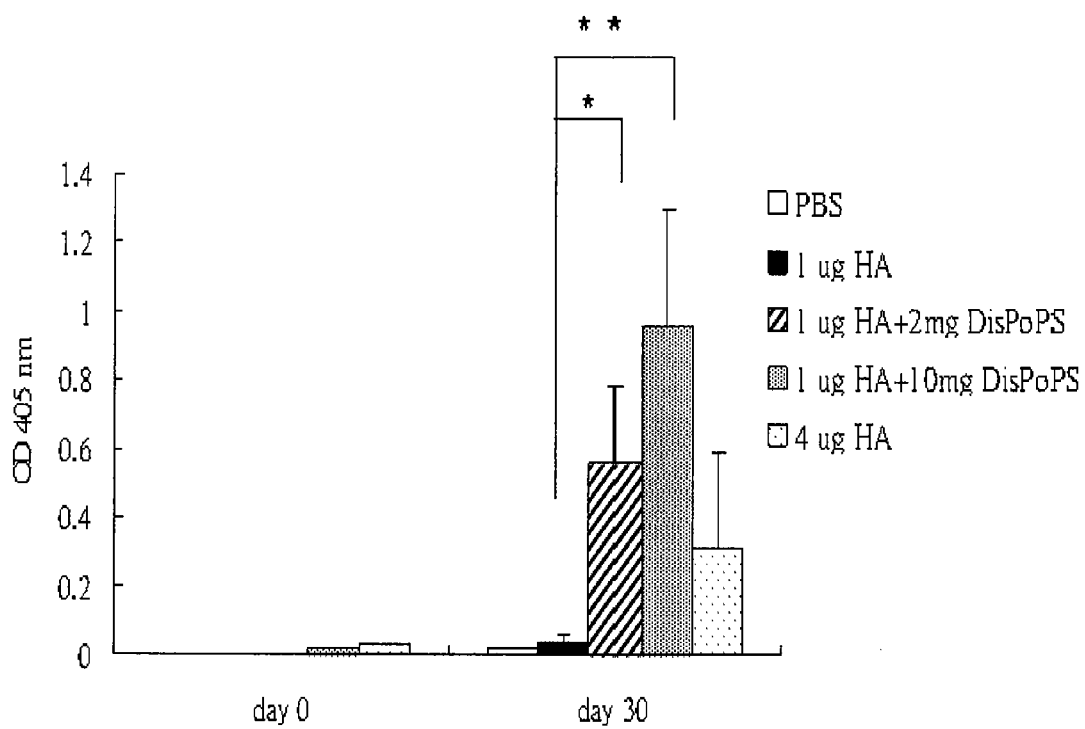
FIG. 15A is a graph showing the effect of *Dioscorea* polysaccharides on stimulating the IgG antibody of blood collected from mice treated as set forth in Example 6. The negative group (n=6, □) was sensitized intranasally with phosphate-buffered saline (PBS). The control group (n=8, ■) was sensitized intranasally with 1 μg hemagglutinin (HA). The treatment groups were sensitized intranasally with 1 μg HA plus 2 mg of *Dioscorea* polysaccharides (DisPoPS) extracted as set forth in Example 1 (n=8, ▨), and with 1 μg HA plus 10 mg of the same polysaccharides extract (n=8, ▩). The positive group was sensitized with 4 μg HA (n=8, ▦). The stimulated level of IgG of the blood collected from the mice at day 0 and day 30 was determined by an enzyme-linked immunosorbent assay (ELISA) and estimated by spectrometer. Asterisks indicate the level of significant difference from the control group: * indicating $p<0.05$; ** indicating $p<0.01$.
Figure 15B:
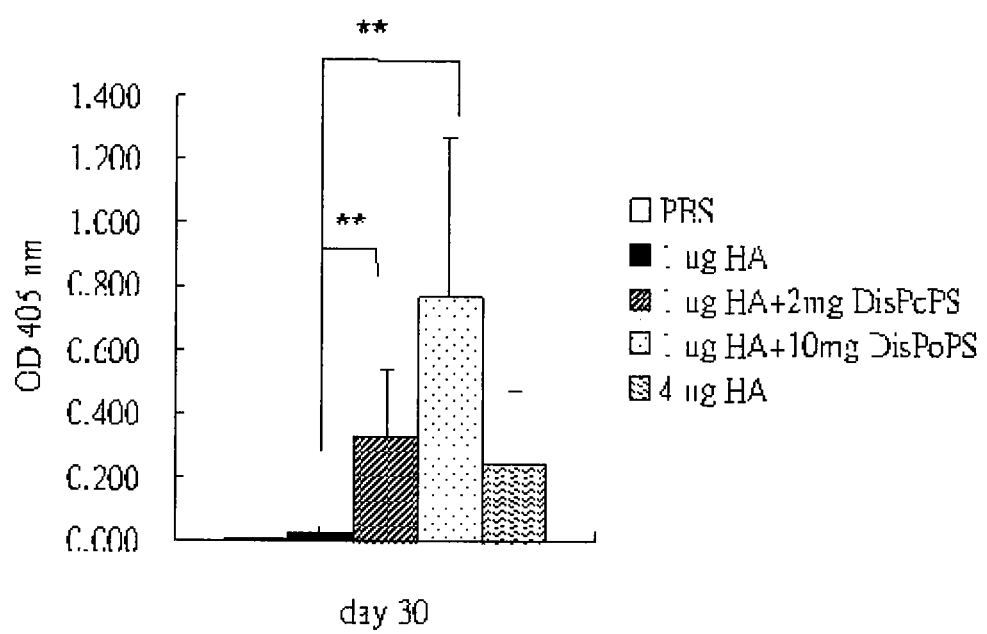
FIG. 15B is a graph showing the effect of *Dioscorea* polysaccharides on stimulating the IgG antibody of the lung wash collected at day 30 from the mice treated as set forth in Example 6. The negative group (n=6, □) was sensitized intranasally with PBS. The control group (n=8, ■) was sensitized intranasally with 1 μg HA. The treatment groups were sensitized intranasally with 1 μg HA plus 2 mg of *Dioscorea* polysaccharides extracted as set forth in Example 1 (n=8, ▨), and with 1 μg HA plus 10 mg of the same polysaccharides extract (n=8, ▩). The positive group was sensitized intranasally with 4 μg HA (n=8, ▦). The stimulated level of IgG was determined by ELISA and estimated by a spectrometer. Asterisks indicate the level of significant difference from the control group: ** indicating $p<0.01$.
Figure 15C:
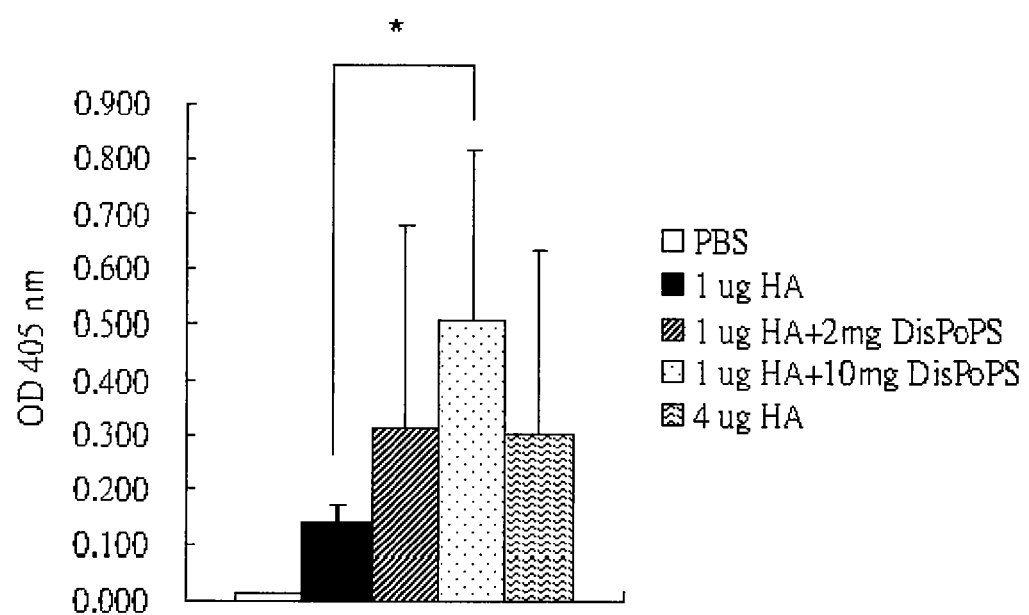
FIG. 15C is a graph showing the effect of *Dioscorea* polysaccharides on stimulating the IgG antibody of the nasal wash collected at day 30 from the mice treated as set forth in Example 6. The negative group (n=6, □) was sensitized intranasally with PBS. The control group (n=8, ■) was sensitized intranasally with 1 μg HA. The treatment groups were sensitized intranasally with 1 μg HA plus 2 mg of *Dioscorea* polysaccharides extracted as set forth in Example 1 (n=8, ▨), and with 1 μg HA plus 10 mg of the same polysaccharides extract (n=8, ▩). The positive group was sensitized intranasally with 4 μg HA (n=8, ▦). The stimulated level of IgG was determined by ELISA and estimated by a spectrometer. Asterisks indicate the level of significant difference from the control group: * indicating $p<0.05$.
Figure 15D:
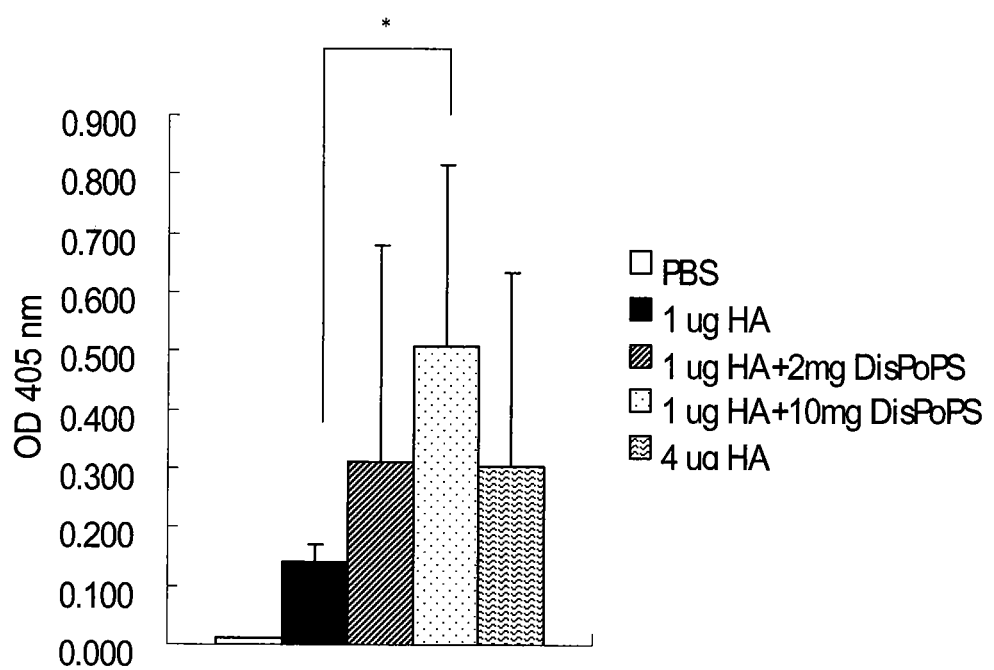
FIG. 15D is a graph showing the effect of *Dioscorea* polysaccharides on stimulating the IgG antibody of the vaginal wash collected at day 30 from the mice treated as set forth in Example 6. The negative group (n=6, □) was sensitized intranasally with PBS. The control group (n=8, ■) was sensitized intranasally with 1 μg HA. The treatment groups were sensitized intranasally with 1 μg HA plus 2 mg of *Dioscorea* polysaccharide extracted as set forth in Example 1 (n=8, ▨), and with 1 μg HA plus 10 mg of the same polysaccharides extract (n=8, ▩). The positive group was sensitized intranasally with 4 μg HA (n=8, ▦). The stimulated level of IgG was determined by ELISA and estimated by a spectrometer. Asterisks indicate the level of significant difference from the control group: * indicating $p<0.05$.
Figure 16A:
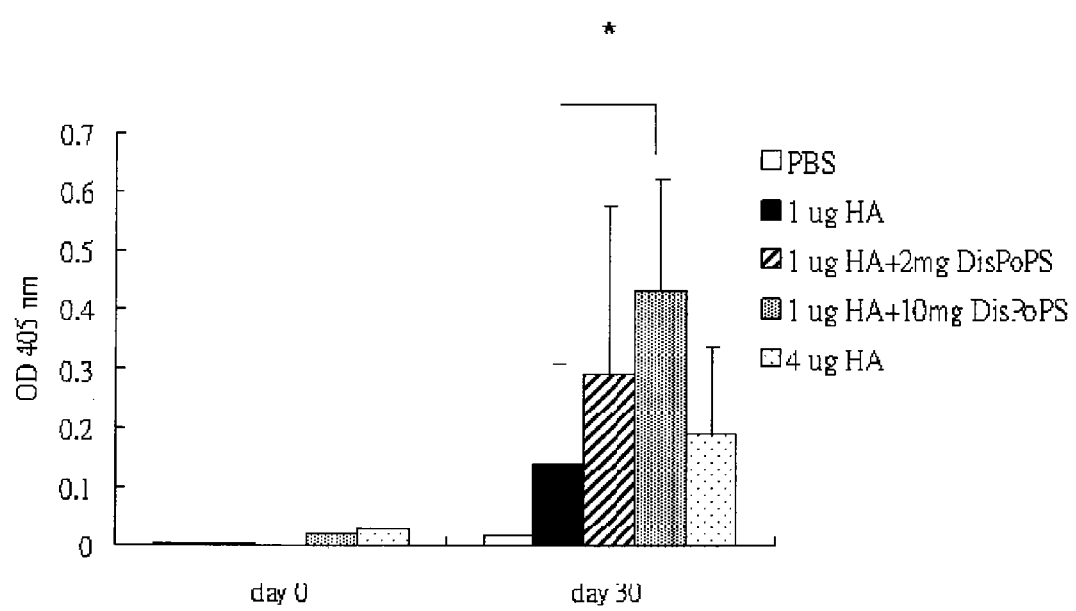
FIG. 16A is a graph showing the effect of *Dioscorea* polysaccharides on stimulating the IgA antibody of blood collected from mice as set forth in Example 6. The negative group (n=6, □) was sensitized intranasally with PBS. The control group (n=8, ■) was sensitized intranasally with 1 μg HA. The treatment groups were sensitized intranasally with 1 μg HA plus 2 mg of *Dioscorea* polysaccharides extracted as set forth in Example 1 (n=8, ▨), and with 1 μg HA plus 10 mg of the same polysaccharides extract (n=8, ▩). The positive group was sensitized intranasally with 4 μg HA (n=8, ▦). The stimulated level of IgA of the blood collected from the mice at day 0 and day 30 was determined by ELISA and estimated by spectrometer. Asterisks indicate the level of significant difference from the control group: * indicating $p<0.05$.
Figure 16B:
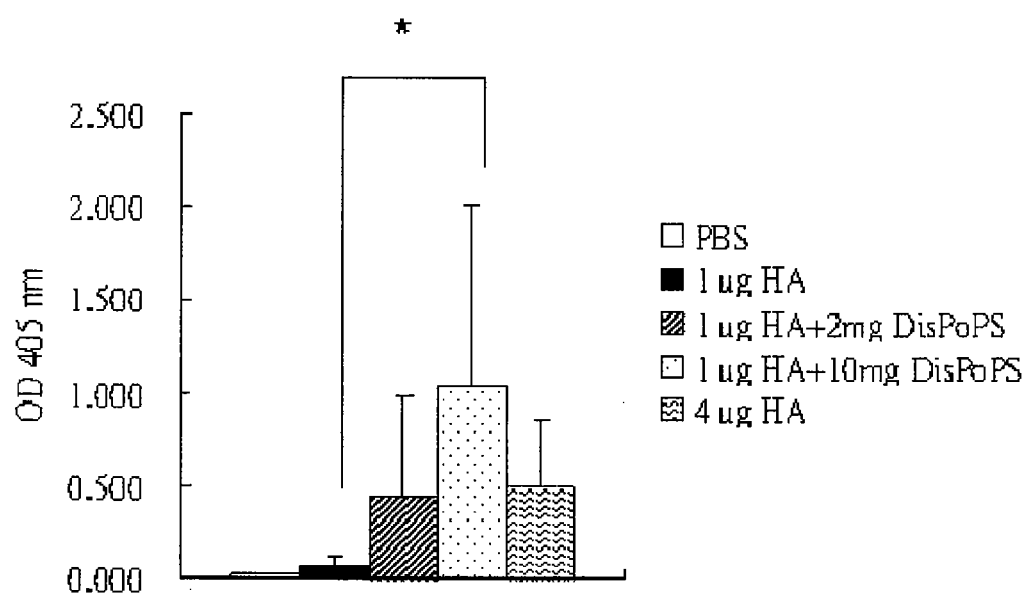
FIG. 16B is a graph showing the effect of *Dioscorea* polysaccharides on stimulating the IgA antibody of the lung wash collected at day 30 from the mice treated as set forth in Example 6. The negative group (n=6, □) was sensitized intranasally with PBS. The control group (n=8, ■) was sensitized intranasally with 1 μg HA. The treatment groups were sensitized intranasally with 1 μg HA plus 2 mg of *Dioscorea* polysaccharides extracted as set forth in Example 1 (n=8, ▨), and with 1 μg HA plus 10 mg of the same polysaccharides extract (n=8, ▩). The positive group was sensitized intranasally with 4 μg HA (n=8, ▦). The stimulated level of IgA was determined by ELISA and estimated by a spectrometer. Asterisks indicate the level of significant difference from the control group: * indicating $p<0.05$.
Figure 16C:
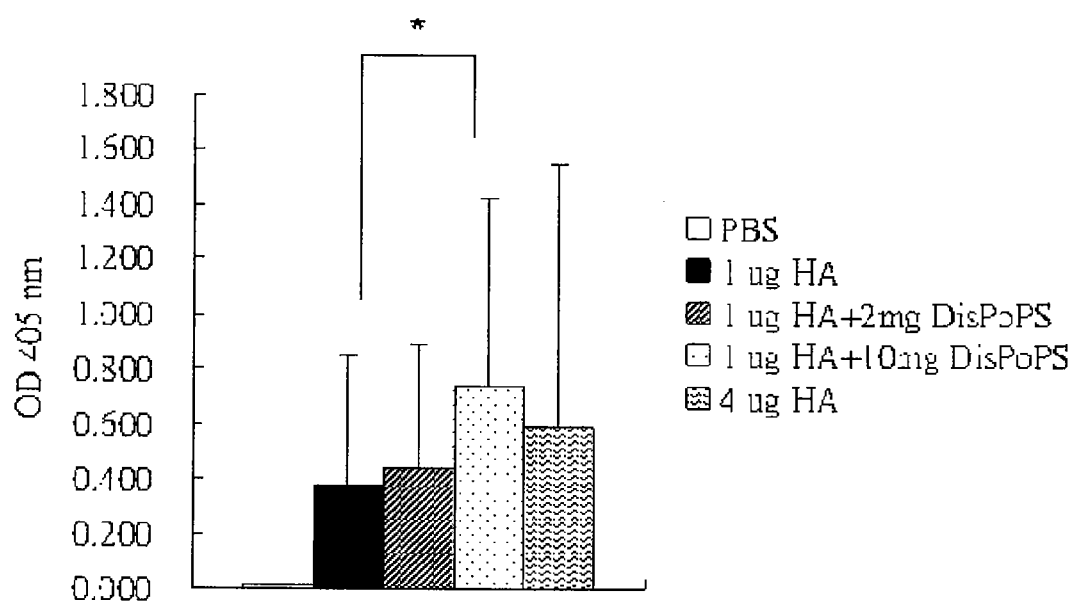
FIG. 16C is a graph showing the effect of *Dioscorea* polysaccharides on stimulating the IgA antibody of the nasal wash collected at day 30 from the mice treated as set forth in Example 6. The negative group (n=6, □) was sensitized intranasally with PBS. The control group (n=8,■) was sensitized intranasally with 1 μg HA. The treatment groups were sensitized intranasally with 1 μg HA plus 2 mg of *Dioscorea* polysaccharides extracted as set forth in Example 1 (n=8, ▨), and with 1 μg HA plus 10 mg of the same polysaccharides extract (n=8, ▭). The positive group was sensitized intranasally with 4 μg HA (n=8, ▩). The stimulated level of IgA was determined by ELISA and estimated by a spectrometer. Asterisks indicate the level of significant difference from the control group: * indicating p<0.05.
Figure 16D:
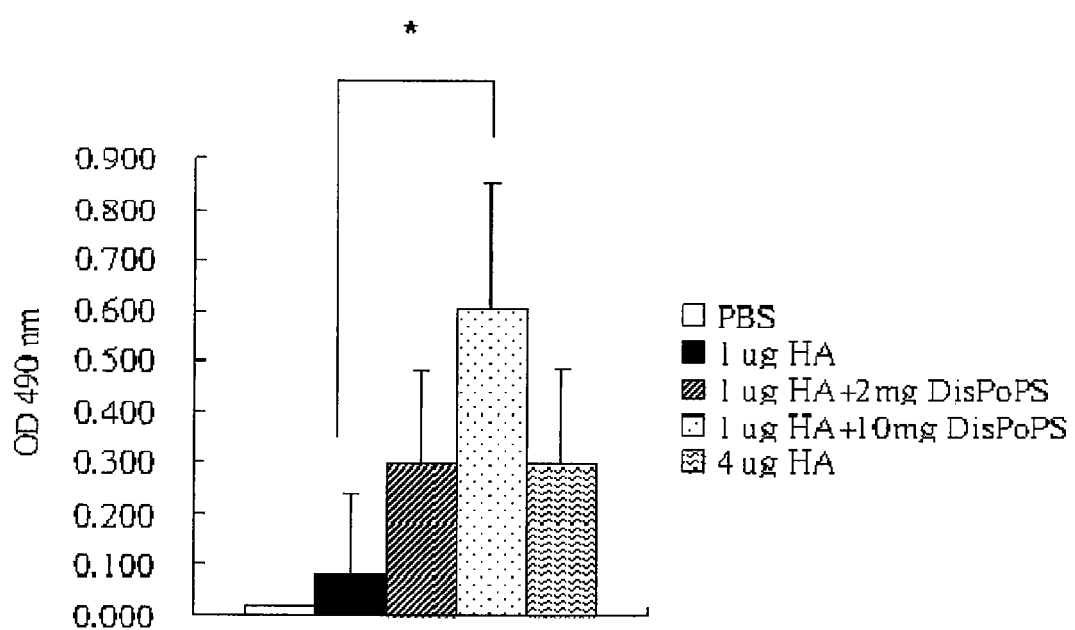
FIG. 16D is a graph showing the effect of *Dioscorea* polysaccharides on stimulating the IgA antibody of the vaginal wash collected at day 30 from the mice treated as set forth in Example 6. The negative group (n=6, □) was sensitized intranasally with PBS. The control group (n=8, ■) was sensitized intranasally with 1 μg HA. The treatment groups were sensitized intranasally with 1 μg HA plus 2 mg of *Dioscorea* polysaccharides extracted as set forth in Example 1 (n=8, ▨), and with 1 μg HA plus 10 mg of the same polysaccharides extract (n=8, ▭). The positive group was sensitized intranasally with 4 μg HA (n=8, ▩). The stimulated level of IgA was determined by ELISA and estimated by a spectrometer. Asterisks indicate the level of significant difference from the control group: * indicating p<0.05.

To investigate the ability of *Dioscorea* polysaccharides to act as an adjuvant, commercial influenza vaccine and *Dioscorea* polysaccharides from Example 2 were mixed to form a vaccine composition and mice were immunized intranasally with the aforementioned composition. Systemic serum (as shown in FIG. 15A) and local (nasal in FIG. 15B, lung in FIG. 15C and vaginal wash in FIG. 15D) IgG antibodies were all significantly stimulated in the group of mice immunized with 1 μg HA and 10 mg of *Dioscorea* polysaccharides. IgG antibodies of serum and lung flushing solution were also significantly stimulated in the group of mice immunized with 1 μg HA and 2 mg of *Dioscorea* polysaccharides from Example 2.

As shown in FIGS. 16A-16D, systemic (serum) and local (nasal, lung and vaginal wash) IgA antibodies are all significantly stimulated in the group of mice immunized with 1 μg HA vaccine and 10 mg *Dioscorea* polysaccharides.

Typically, influenza viruses bind through hemagglutinin onto sialic acid sugars on the surfaces of epithelial cells; typically in the nose, throat and lungs of mammals. In the present invention, *Dioscorea* polysaccharides enhanced anti-HA antibodies at mucosal sites. Therefore, the mammals' bodies could neutralize the viruses at the first line in the mucous membranes and prevent the viral infections. The mice studies of the present inventions are considered to be representative of effectiveness of the use of the polysaccharides as vaccine adjutants in humans. As used herein, "subject" means mammals, including humans. It is reasonably believed that the adjuvant of the present invention would be effective against a number of viruses and other pathogens adversely affecting humans, including the cold virus. Moreover, *Dioscorea* polysaccharides have low toxicity compared to cholera toxin and *E. coli* heat-labile enterotoxin and have great potential to break though the tolerance in mucosal sites.

As used herein, the singular includes the plural and the plural includes the singular, unless otherwise specifically stated or clear from the context.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method of inducing mucosal immune responses to an antigen in a subject in need thereof comprising administering to a mucosal site of said subject a vaccine comprising said antigen in combination with an adjuvant, wherein the *Dioscorea* polysaccharide (1) is characterized by a Fourier transform infrared (FT-IR) spectrum with peaks at 3000-2850 $cm^{-1}$, 1050-1020 $cm^{-1}$, 1085-1075 $cm^{-1}$, 1155-1150 $cm^{-1}$ and 845-830 $cm^{-1}$, (2) is primarily composed of α-pyranosides and (3) is prepared by a process comprising the steps of:

(a) eliminating small molecules by immersing a *Dioscorea* sp. in a 40% (v/v) alcoholic solution to obtain an insoluble solid portion;

(b) de-starching the insoluble solid portion obtained in step (a) in a water solution by a starch-hydrolyzing enzyme to obtain an aqueous solution;

(c) treating the aqueous solution obtained in step (b) with a 75% (v/v) alcoholic solution to obtain a precipitated solid portion including the *Dioscorea* polysaccharide; and (d) removing all protein substances from the precipitated solid portion obtained in step (c) with a deproteinizing agent.

2. The method according to claim 1, wherein the *Dioscorea* polysaccharide is further characterized by a FT-IR spectrum as of FIG. 1.

3. The method according to claim 1, wherein the alcoholic solution is 40% (v/v) methanol or ethanol.

4. The method according to claim 1, wherein the administration is oral or intranasal administration.

5. The method according to claim 1, wherein a mucosal immune response is induced or enhanced at a plurality of mucosal sites.

6. The method according to claim 5, wherein the mucosal site includes one or more sites selected from the group consisting of oral, buccal, esophageal, gastric, endometrial, nasal, lung, respiratory tract, ocular, intestinal and vaginal sites.

7. The method according to claim 1, wherein the antigen is a viral, a bacterial, a fragment thereof, or a portion of a pathogen's structure.

8. The method according to claim 1, wherein the mucosal immune responses comprise either or both of IgA and IgG antibody responses.

9. The method according to claim 1, wherein the administration of the vaccine in combination with the *Dioscorea* polysaccharide induces mucosal immune responses breaking immunological tolerance in said subject.

10. The method according to claim 1, wherein the *Dioscorea* sp. is *Dioscorea alata*.

* * * * *

SEQUENCE LISTING

<160> NUMBER OF SEQ ID NOS: 12

<210> SEQ ID NO 1
<211> LENGTH: 25
<212> TYPE: DNA
<213> ORGANISM: Artificial

```
<220> FEATURE:
<223> OTHER INFORMATION: primer

<400> SEQUENCE: 1
atggacactg ttcctgaact caact                                              25

<210> SEQ ID NO 2
<211> LENGTH: 26
<212> TYPE: DNA
<213> ORGANISM: Artificial
<220> FEATURE:
<223> OTHER INFORMATION: primer

<400> SEQUENCE: 2
caggacaggt atagattctt tcctttt                                            26

<210> SEQ ID NO 3
<211> LENGTH: 23
<212> TYPE: DNA
<213> ORGANISM: Artificial
<220> FEATURE:
<223> OTHER INFORMATION: primer

<400> SEQUENCE: 3
atgggtctca accccagct agt                                                 23

<210> SEQ ID NO 4
<211> LENGTH: 24
<212> TYPE: DNA
<213> ORGANISM: Artificial
<220> FEATURE:
<223> OTHER INFORMATION: primer

<400> SEQUENCE: 4
gctctttagg ctttccagga agtc                                               24

<210> SEQ ID NO 5
<211> LENGTH: 24
<212> TYPE: DNA
<213> ORGANISM: Artificial
<220> FEATURE:
<223> OTHER INFORMATION: primer

<400> SEQUENCE: 5
atgaagttcc tctctgcaag agac                                               24

<210> SEQ ID NO 6
<211> LENGTH: 24
<212> TYPE: DNA
<213> ORGANISM: Artificial
<220> FEATURE:
<223> OTHER INFORMATION: primer

<400> SEQUENCE: 6
cactaggttt gccgagtaga tctc                                               24

<210> SEQ ID NO 7
<211> LENGTH: 24
<212> TYPE: DNA
<213> ORGANISM: Artificial
<220> FEATURE:
<223> OTHER INFORMATION: primer

<400> SEQUENCE: 7
tgaacgctac acactgcatc ttgg                                               24
```

```
<210> SEQ ID NO 8
<211> LENGTH: 23
<212> TYPE: DNA
<213> ORGANISM: Artificial
<220> FEATURE:
<223> OTHER INFORMATION: primer

<400> SEQUENCE: 8 cgactcctttt tccgcttcct gag                                              23

<210> SEQ ID NO 9
<211> LENGTH: 41
<212> TYPE: DNA
<213> ORGANISM: Artificial
<220> FEATURE:
<223> OTHER INFORMATION: primer

<400> SEQUENCE: 9
tggaccgcaa caacgccatc tatgccatct atgagaaaac c                           41

<210> SEQ ID NO 10
<211> LENGTH: 32
<212> TYPE: DNA
<213> ORGANISM: Artificial
<220> FEATURE:
<223> OTHER INFORMATION: primer

<400> SEQUENCE: 10
tggagctgaa gcaatagttg gtatccaggg ct                                     32

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
gactacctca tgaagatcct                                                   20

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
ccacatctgc tggaaggtgg                                                   20
```